US012616220B2

(12) United States Patent
Sugahara et al.

(10) Patent No.: US 12,616,220 B2
(45) Date of Patent: May 5, 2026

(54) METHOD FOR PRODUCING PLANT-BASED MILK-FERMENTED LIQUID

(71) Applicant: Asahi Group Holdings, Ltd., Tokyo (JP)

(72) Inventors: Hirosuke Sugahara, Ibaraki (JP); Sayaka Nagaosa, Ibaraki (JP); Keitaro Nagayama, Ibaraki (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 272 days.

(21) Appl. No.: 18/283,335

(22) PCT Filed: Mar. 10, 2022

(86) PCT No.: PCT/JP2022/010661
§ 371 (c)(1),
(2) Date: Sep. 21, 2023

(87) PCT Pub. No.: WO2022/202372
PCT Pub. Date: Sep. 29, 2022

(65) Prior Publication Data
US 2024/0172767 A1 May 30, 2024

(30) Foreign Application Priority Data
Mar. 25, 2021 (JP) ................................. 2021-052277

(51) Int. Cl.
*A23C 11/10* (2025.01)
*A23L 2/38* (2021.01)
(Continued)

(52) U.S. Cl.
CPC .............. *A23C 11/10* (2013.01); *A23L 2/382* (2013.01); *A23L 5/28* (2016.08); *A23L 7/104* (2016.08);
(Continued)

(58) Field of Classification Search
CPC . A23C 11/10; A23L 7/104; A23L 5/28; A23L 2/382; C12N 1/205; C12R 2001/225
(Continued)

(56) References Cited

U.S. PATENT DOCUMENTS

| 4,744,992 A | 5/1988 | Mitchell et al. |
| 2015/0322496 A1 | 11/2015 | Hyakutake et al. |
| 2021/0386084 A1 | 12/2021 | Tropel |

FOREIGN PATENT DOCUMENTS

| CA | 2 897 606 | 7/2014 |
| CN | 109337833 | 2/2019 |

(Continued)

OTHER PUBLICATIONS

Translation of KR-20200000733-A (Year: 2020).*
(Continued)

*Primary Examiner* — Brent T O'Hern
(74) *Attorney, Agent, or Firm* — Wenderoth, Lind & Ponack, L.L.P.

(57) ABSTRACT
Provided is a method for producing a plant-based milk-fermented liquid having reduced plant smell. The method includes bringing a plant-based milk into contact with a lactic acid bacterial strain(s) including at least one selected from the group consisting of the *Lactobacillus fermentum* CP1299 strain, the *Lactobacillus fermentum* CP3024 strain, the *Lactobacillus reuteri* CP3017 strain, and the *Lactobacillus reuteri* CP3019 strain.

6 Claims, 8 Drawing Sheets

(51) Int. Cl.

| | | |
|---|---|---|
| *A23L 5/20* | (2016.01) | |
| *A23L 7/104* | (2016.01) | |
| *C12N 1/205* | (2026.01) | |
| *C12R 1/225* | (2006.01) | |

(52) U.S. Cl.
CPC ........ *C12N 1/205* (2021.05); *C12R 2001/225* (2021.05)

(58) Field of Classification Search
USPC .......................................................... 426/18
See application file for complete search history.

(56) References Cited

FOREIGN PATENT DOCUMENTS

| | | | | |
|---|---|---|---|---|
| CN | 107118975 | 8/2020 | | |
| JP | 62-87070 | 4/1987 | | |
| JP | 9-205999 | 8/1997 | | |
| JP | 2003-284520 | 10/2003 | | |
| JP | 2006-290835 | 10/2006 | | |
| JP | 2014-217372 | 11/2014 | | |
| JP | 2020-17 | 1/2020 | | |
| KR | 20200000733 A * | 1/2020 | ............ | A23L 29/00 |
| WO | 2009/065722 | 5/2009 | | |
| WO | 2010/136321 | 12/2010 | | |
| WO | WO-2010136321 A1 * | 12/2010 | ............... | A23L 2/66 |
| WO | 2019/132233 | 7/2019 | | |
| WO | 2020/070045 | 4/2020 | | |

OTHER PUBLICATIONS

Kahn et al., "Co-culture submerged fermentation by lactobacillus and yeast more effectively improved the profiles and bioaccessibility of phenolics in extruded brown rice than single-culture fermentation", Food Chemistry, 2020, vol. 326, , 126985, pp. 1-8.

Do Espirito-Santo et al., "Influence of cofermentation by amylolytic *Lactobacillus* strains and probiotic bacteria on the fermentation process, viscosity and microstructure of gruels made of rice, soy milk and passion fruit fiber", Food Research International, 2014, vol. 57, pp. 104-113.

Park et al., "Distinctive Formation of Volatile Compounds in Fermented Rice Inoculated by Different Molds, Yeasts, and Lactic Acid Bacteria", Molecules, 2019, vol. 24, 2123, pp. 1-15.

International Search Report issued May 24, 2022 in corresponding International (PCT) Application No. PCT/JP2022/010661.

International Search Report issued May 24, 2022 in corresponding International (PCT) Application No. PCT/JP2022/010662.

International Preliminary Report on Patentability issued Sep. 12, 2023 in corresponding International (PCT) Application No. PCT/JP2022/010661.

International Preliminary Report on Patentability issued Sep. 12, 2023 in corresponding International (PCT) Application No. PCT/JP2022/010662.

Extended European Search Report issued Mar. 24, 2025 in the European Patent Application No. 22775164.1.

Extended European Search Report issued Mar. 24, 2025 in the European Patent Application No. 22775165.8.

Sang Mi Lee et al., "Volatile Compounds Produced by *Lactobacillus paracasei* During Oat Fermentation", Journal of Food Science, vol. 81, No. 12, 2016, pp. C2915-C2922.

Office Action issued Sep. 16, 2025 in United States U.S. Appl. No. 18/283,358.

Da Lorn, "Screening of lactic acid bacteria for their use as aromatic starters during fermentation of vegetables", Agricultural sciences, Universite Bourgogne Franche-Comte, English, 2020, 159 pages.

Qingyu Zhao, et al., "Changes in flavor of fragrant rice during storage under different conditions", J Sci Food Agric, 2020, vol. 100, pp. 3435-3444.

Final Office Action issued Mar. 18, 2026 in U.S. Appl. No. 18/283,358, pp. 1-13.

* cited by examiner

* p < 0.05 vs. *L.brevis T*

* p < 0.05 vs. *L.brevis T*

* p < 0.05 vs. *L.brevis T*

* p < 0.05 vs. *L.gasseri T*

* p < 0.05 vs. *L.gasseri T*

* p < 0.05 vs. *L.gasseri T*

* p < 0.05 vs. *L.gasseri T*

* p < 0.05 vs. *L.gasseri T*

* p < 0.05 vs. *L.gasseri T*

* p < 0.05 vs. *L.gasseri T*

* p < 0.05 vs. *L.gasseri T*

* p < 0.05 vs. *L. gasseri T*

* p < 0.05 vs. *L. gasseri T*

METHOD FOR PRODUCING PLANT-BASED MILK-FERMENTED LIQUID

TECHNICAL FIELD

The present invention relates to a method for producing a plant-based milk-fermented liquid.

BACKGROUND ART

Plant-based milk is a product prepared by size reduction and liquefaction of a plant material such as rice, wheat, or soybeans (see, for example, J. Food Sci. Technol (September 2016) 53(9): 3408-3423). Examples of plant-based milk include rice milk, which is a food prepared by saccharifying rice with enzyme, malted rice (koji), and/or the like, seasoning the saccharified rice by addition of a vegetable oil and/or the like, and then making the resulting product into the form of a milk.

In general, plant-based milk contains aldehydes as flavor components. Aldehydes may be favorable flavor components in beverages having plant flavors. However, in beverages having fermented-milk-like flavors, aldehydes are known to be a cause of unpleasant odors due to unfavorable plant odors. Examples of methods of reducing the amount of aldehydes contained in plant-based milk include the following methods.

For example, JP H9-205999 A describes a method in which the lactic acid bacterium *Leuconostoc mesenteroides* or the lactic acid bacterium *Lactobacillus brevis* is brought into contact with a food containing medium-chain aldehydes while preventing the growth of the lactic acid bacterium, to cause reduction of the medium-chain aldehydes to alcohols. Further, JP 2020-17 A describes a lactic acid fermented beverage obtained by subjecting a plant-based milk obtained using a rice material to lactic acid fermentation using the lactic acid bacterium *Lactobacillus sakei* strain No. 7 or the lactic acid bacterium *Lactobacillus sakei* strain No. 16, and describes that the beverage contained reduced amounts of diacetyl and hexanal.

SUMMARY OF THE INVENTION

Problems to be Solved by the Invention

An object of the present invention is to provide a method for producing a plant-based milk-fermented liquid with reduced plant odor.

Means for Solving Problems

The present invention provides a method for producing a plant-based milk-fermented liquid, the method including bringing a plant-based milk into contact with a lactic acid bacterial strain(s) including at least one selected from the group consisting of the *Lactobacillus fermentum* CP1299 strain, the *Lactobacillus fermentum* CP3024 strain, the *Lactobacillus reuteri* CP3017 strain, and the *Lactobacillus reuteri* CP3019 strain.

In an embodiment, the plant-based milk in the production method may be derived from a cereal. In an embodiment, the plant-based milk in the production method may be derived from rice. In an embodiment, the plant-based milk in the production method may be a saccharified plant-based milk. In an embodiment, the contact between the lactic acid bacterial strain(s) and the plant-based milk in the production method may involve fermentation of the plant-based milk by the lactic acid bacterial strain(s).

The present invention provides a method for reducing the amount of aldehyde in a plant-based milk, the method including bringing a plant-based milk containing aldehyde into contact with a lactic acid bacterial strain(s) including at least one selected from the group consisting of the *Lactobacillus fermentum* CP1299 strain, the *Lactobacillus fermentum* CP3024 strain, the *Lactobacillus reuteri* CP3017 strain, and the *Lactobacillus reuteri* CP3019 strain.

In an embodiment, the plant-based milk in the reducing method may be derived from a cereal. In an embodiment, the plant-based milk in the reducing method may be derived from rice. In an embodiment, the plant-based milk in the reducing method may be a saccharified plant-based milk. In an embodiment, the contact between the lactic acid bacterial strain(s) and the plant-based milk in the reducing method may involve fermentation of the plant-based milk by the lactic acid bacterial strain(s).

The present invention also provides the *Lactobacillus fermentum* CP3024 strain of the accession number: NITE BP-3428, the *Lactobacillus reuteri* CP3017 strain of the accession number: NITE BP-3426, and the *Lactobacillus reuteri* CP3019 strain of the accession number: NITE BP-3427.

Advantageous Effects of the Invention

According to the present invention, a method for producing a plant-based milk-fermented liquid with reduced plant odor may be provided.

MODE FOR CARRYING OUT THE INVENTION

Figure 1:
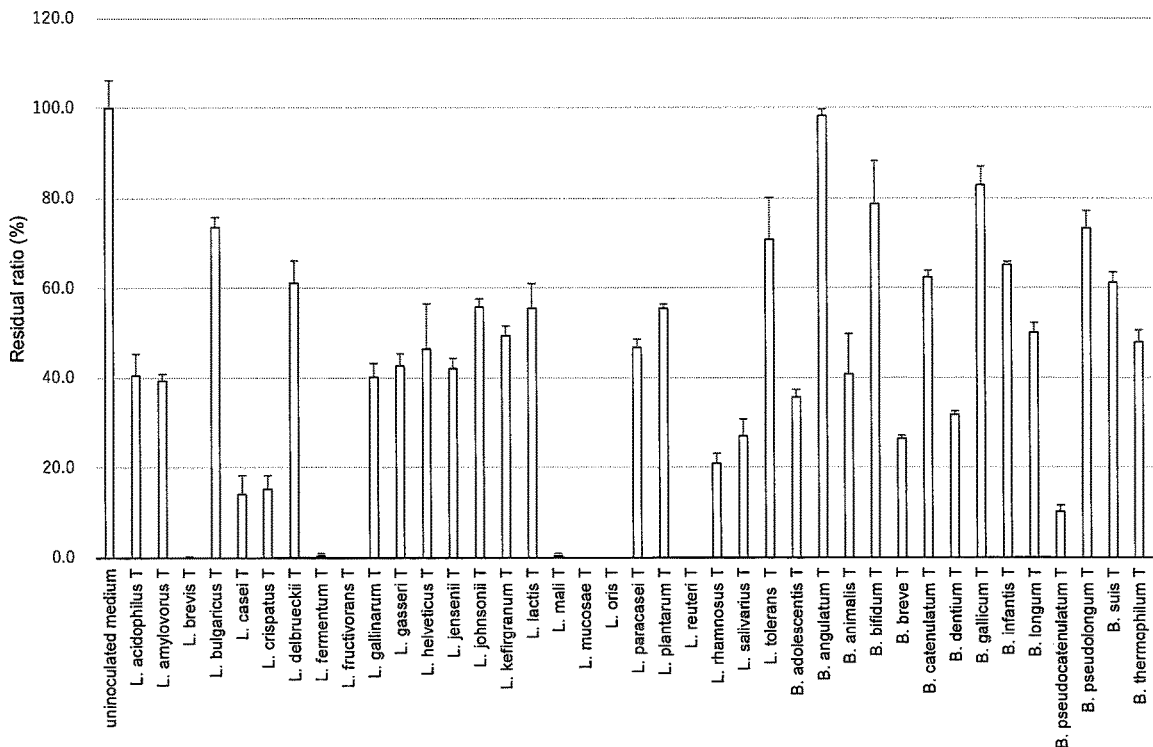
FIG. 1 is a graph showing the abilities of lactic acid bacteria to reduce the amount of acetaldehyde at low concentration.

In the present specification, the term "step" includes not only an independent step, but also a step that is not clearly distinguishable from another step, as long as the desired purpose of the step can be achieved. Unless otherwise specified, when a plurality of substances corresponding to a certain component is present in a composition, the content of the component in the composition means the total amount of the plurality of substances present in the composition. The upper limit and lower limit of a numerical range described in the present description may be an arbitrary combination of values selected from those exemplified for the numerical range. Embodiments of the present invention are described below in detail. The embodiments described below, however, are merely examples of methods of producing a plant-based milk-fermented liquid for realization of the technological thought of the present invention. Therefore, the present invention is not limited to the methods of producing a plant-based milk-fermented liquid described below.

Method for Producing Plant-Based Milk-Fermented Liquid

The method for producing a plant-based milk-fermented liquid includes bringing a plant-based milk into contact with a lactic acid bacterial strain(s) including at least one selected from the group consisting of the *Lactobacillus fermentum* CP1299 strain, the *Lactobacillus fermentum* CP3024 strain, the *Lactobacillus reuteri* CP3017 strain, and the *Lactobacillus reuteri* CP3019 strain.

By bringing a particular lactic acid bacterial strain(s) into contact with a plant-based milk, the content of aldehyde in the plant-based milk may be effectively reduced to reduce the plant odor derived from the aldehyde, to enable production of a plant-based milk-fermented liquid having an excellent yogurt-like flavor. The plant-based milk-fermented liquid produced has an excellent balance between sweetness and sourness, and an improved mellow taste as a fermented milk. This may be thought to be due to, for example, the excellent activity of the particular lactic acid bacterial strain(s) to reduce the amount of aldehyde contained in the plant-based milk.

In the method for producing a plant-based milk-fermented liquid, the content of aldehyde in a plant-based milk may be reduced by bringing a particular lactic acid bacterium/bacteria into contact with the plant-based milk. In other words, the method for producing a plant-based milk-fermented liquid may be a method for reducing the amount of aldehyde in a plant-based milk.

Lactic Acid Bacterial Strains

In the method for producing a plant-based milk-fermented liquid, a particular lactic acid bacterial strain(s) is/are used. The particular lactic acid bacterial strain(s) include(s) at least one selected from the group consisting of the *Lactobacillus fermentum* CP1299 strain, the *Lactobacillus fermentum* CP3024 strain, the *Lactobacillus reuteri* CP3017 strain, and the *Lactobacillus reuteri* CP3019 strain. The *Lactobacillus fermentum* CP1299 strain herein is a lactic acid bacterium belonging to *Lactobacillus fermentum*, and has been internationally deposited with Patent Microorganisms Depositary, NITE National Institute of Technology and Evaluation (Room 122, 2-5-8 Kazusakamatari, Kisarazu-shi, Chiba, 292-0818 Japan), which is an international depository institution in accordance with the Budapest Treaty, under the accession number: NITE BP-1512 as of Jan. 18, 2013. The *Lactobacillus fermentum* CP3024 strain is a lactic acid bacterium belonging to *Lactobacillus fermentum*, and has been internationally deposited under the accession number: NITE BP-03428 as of Mar. 1, 2021. The *Lactobacillus reuteri* CP3017 strain is a lactic acid bacterium belonging to *Lactobacillus reuteri*, and has been internationally deposited under the accession number: NITE BP-03426 as of Mar. 1, 2021. The *Lactobacillus reuteri* CP3019 strain is a lactic acid bacterium belonging to *Lactobacillus reuteri*, and has been internationally deposited under the accession number: NITE BP-03427 as of Mar. 1, 2021.

In the method for producing a plant-based milk-fermented liquid, the particular lactic acid bacterium/bacteria may be used in combination with other lactic acid bacteria, bifidobacteria, and the like. Examples of the lactic acid bacteria and bifidobacteria other than the particular lactic acid bacterium/bacteria include the genus *Lactobacillus*, such as *Lactobacillus fermentum* (for example, the JCM1173 strain) other than the CP1299 strain and the CP3024 strain, *Lactobacillus reuteri* (for example, the JCM1112 strain) other than the CP3017 strain and the CP3019 strain, *Lactobacillus gasseri, Lactobacillus oris, Lactobacillus mucosae, Lactobacillus fructivorans, Lactobacillus casei, Lactobacillus delbrueckii, Lactobacillus bulgaricus, Lactobacillus helveticus, Lactobacillus brevis, Lactobacillus plantarum, Lactobacillus lactis, Lactobacillus acidophilus, Lactobacillus amylovorus, Lactobacillus crispatus, Lactobacillus gallinarum, Lactobacillus jensenii, Lactobacillus johnsonii, Lactobacillus kefirgranum, Lactobacillus mali, Lactobacillus paracasei, Lactobacillus rhamnosus, Lactobacillus salivarius,* and *Lactobacillus tolerans*; the genus *Bifidobacterium,* such as *Bifidobacterium adolescentis, Bifidobacterium angulatum, Bifidobacterium animalis, Bifidobacterium bifidum, Bifidobacterium breve, Bifidobacterium catenulatum, Bifidobacterium dentium, Bifidobacterium gallicum, Bifidobacterium infantis, Bifidobacterium longum, Bifidobacterium pseudocatenulatum, Bifidobacterium pseudolongum, Bifidobacterium suis,* and *Bifidobacterium thermophilum*; the genus *Streptococcus,* such as *Streptococcus thermophilus, Streptococcus lactis, Streptococcus cremoris, Streptococcus faecalis,* and *Streptococcus faecium*; the genus *Leuconostoc,* such as *Leuconostoc mesenteroides, Leuconostoc dextranicum, Leuconostoc cremoris,* and *Leuconostoc oenos*; and the genus *Pediococcus,* such as *Pediococcus cerevisiae, Pediococcus acidilactici,* and *Pediococcus halophilus.*

In cases where the lactic acid bacterium/bacteria used in the method for producing a plant-based milk-fermented liquid include(s) at least one lactic acid bacterium other than the particular lactic acid bacterium/bacteria, and at least one

*Bifidobacterium*, its/their content ratio may be not more than 50%, preferably not more than 10%, or less than 5% with respect to the total of the lactic acid bacterium and/or *Bifidobacterium*. The content ratio of the lactic acid bacterium and/or *Bifidobacterium* may be determined from the number of bacterial cells of the at least one lactic acid bacterium and/or *Bifidobacterium* used. Alternatively, in cases where a preculture is used as the at least one lactic acid bacterium and/or *Bifidobacterium*, the content ratio may be determined based on the volume of the preculture.

Plant-Based Milk

The plant-based milk may be a product prepared by size reduction and liquefaction of a plant material by physical crushing, and/or saccharification using an enzyme, malted rice, and/or the like. The plant-based milk may be a product prepared by liquefaction of a plant material by a known method, or may be a product selected from commercially available products as appropriate. Examples of the plant material include cereals such as rice, barley, wheat, oats, rye, soybeans, and peanuts; nuts and seeds such as almonds, coconuts, cashew nuts, macadamia nuts, and walnuts; and vegetables such as carrot, potato, sweet potato, cassava, and tomato. In particular, the plant material preferably contains a cereal since a cereal contains a large amount of carbohydrates. The plant material more preferably contains at least one selected from the group consisting of at least rice and barley, still more preferably contains at least rice or barley.

In cases where rice is used as the plant material, the rice may be at least one selected from the group consisting of unhulled rice, brown rice (including germinated brown rice), polished rice, red bran (akanuka), middle bran (chunuka), white bran (shironuka), and higher white bran (joshironuka). Examples of the polished rice include those with different degrees of polishing, such as 30%-polished rice, 50%-polished rice, 70%-polished rice, and white rice, and the polished rice may contain residual germs. The rice as the plant material is preferably at least one selected from the group consisting of brown rice, polished rice, middle bran, and higher white bran, more preferably at least one selected from the group consisting of brown rice, polished rice, and higher white bran. The rice is still more preferably brown rice or white rice. The rice as the plant material may be pulverized to a predetermined grain size by a known method, or the pulverization may be omitted to leave the rice as it is. The rice may also be in a state where it has been saccharified by a microorganism, an enzyme treatment, and/or the like. Depending on the starch contained, rice may be classified into non-glutinous rice, glutinous rice, and the like. Any of these may be used. In cases where the plant material contains rice, plant materials other than rice may also be contained. The plant material may contain, in addition to rice, for example, other cereals such as barley, wheat, oats, rye, soybeans, and peanuts; and nuts and seeds such as almonds, coconuts, cashew nuts, macadamia nuts, and walnuts. The content of the other cereals and the like in the plant material containing rice may be, for example, not more than 30% by mass, not more than 20% by mass, or not more than 10% by mass. The lower limit of the content of the other cereals and the like in the plant material containing rice may be, for example, not less than 0.1% by mass or not less than 1% by mass.

In cases where barley is used as the plant material, it may be at least one selected from the group consisting of two-rowed barley, four-rowed barley, six-rowed barley, naked barley, and wild barley, or may be at least one selected from the group consisting of two-rowed barley and six-rowed barley. The barley as the plant material may be pulverized to a predetermined grain size by a known method, or the pulverization may be omitted to leave the barley as it is. The barley may be in a state where it has been saccharified by a microorganism, an enzyme treatment, and/or the like. In cases where the plant material contains barley, the plant material may also contain plant materials other than barley. The plant material may contain, in addition to barley, for example, other cereals such as rice, wheat, oats, rye, soybeans, and peanuts; and nuts and seeds such as almonds, coconuts, cashew nuts, macadamia nuts, and walnuts. The content of the other cereals and the like in the plant material containing barley may be, for example, not more than 30% by mass, not more than 20% by mass, or not more than 10% by mass. The lower limit of the content of the other cereals in the plant material containing barley may be, for example, not less than 0.1% by mass or not less than 1% by mass.

The plant-based milk may be, for example, a product prepared by performing saccharification treatment in which, for example, starch contained in the plant material (preferably a cereal) is hydrolyzed by the use of an appropriate enzyme. In other words, the plant-based milk may be a saccharified plant-based milk, and is preferably a plant-based milk prepared, from the viewpoint of increasing the monosaccharide content, by subjecting a plant-based milk that uses rice as a plant material to saccharification treatment. The plant-based milk is more preferably a plant-based milk prepared by subjecting a plant-based milk that uses brown rice or white rice as a plant material to saccharification treatment. As the enzyme in the saccharification treatment, for example, α-amylase (EC 3.2.1.1) may be used. The amount of the enzyme added may be, for example, 0.01% to 1% with respect to the mass of the plant material. The conditions of the hydrolysis reaction may be appropriately selected in accordance with, for example, the enzyme and the plant material used. The reaction temperature may be, for example, 40° C. to 100° C., preferably 50° C. to 70° C. The reaction time may be, for example, 1 hour to 24 hours, preferably 2 hours to 12 hours.

In the preparation of the plant-based milk by saccharification treatment, hydrolysis with α-amylase may be further followed by saccharification with glucoamylase (EC 3.2.1.3) or the like. The plant-based milk may be a product obtained by saccharification treatment in which malted rice or the like is allowed to act on the plant material.

The plant-based milk prepared by the saccharification treatment contains various saccharides including monosaccharides such as glucose, disaccharides such as maltose, trisaccharides such as maltotriose, and tetra- and higher saccharides. The saccharide composition of the plant-based milk is preferably a glucose-rich composition since, while glucose is degraded by a lactic acid bacterium in the later-described fermentation step, glucose eventually becomes the main source of sweetness. The content of monosaccharides such as glucose may be, for example, not less than 30% by mass, preferably not less than 50% by mass, more preferably not less than 70% with respect to the total saccharides contained in the plant-based milk.

The plant-based milk may be in the form of, for example, a milk-like emulsion. After the size reduction and liquefaction of the plant material, the plant-based milk may be seasoned with a vegetable oil, an animal oil, salt, sugar, amino acid, a flavor, a thickener, a thickening agent, an emulsifier, a pH-adjusting agent, and/or the like.

Aldehydes

Plant-based milk contains aldehydes derived from a plant material. The aldehydes may have, for example, a plant-odor-like flavor. Examples of the aldehydes include aliphatic aldehydes such as short-chain aliphatic aldehydes, medium-chain aliphatic aldehydes, and long-chain aliphatic aldehydes; and aromatic aldehydes. Short-chain aliphatic aldehydes have not more than 5 carbon atoms; medium-chain aliphatic aldehydes have 6 to 12 carbon atoms; and long-chain aliphatic aldehydes have not less than 13 carbon atoms. Specific examples of the aliphatic aldehydes include acetaldehyde, malondialdehyde, butanal, 2-methylpropanal, pentanal, 2-methylbutanal, 3-methylbutanal, hexanal, crotonaldehyde, 4-hydroxy-2-hexenal, 4-hydroxy-2-nonenal, 2,4-nonadienal, heptanal, octanal, nonanal, decanal, 2,4-decadienal, and tetradecanal. Specific examples of the aromatic aldehydes include benzaldehyde, anisaldehyde, and cuminaldehyde.

The aldehyde whose content is to be reduced by the method for producing a plant-based milk-fermented liquid may be aliphatic aldehydes and aromatic aldehydes, or may be at least one selected from a group consisting of short-chain aliphatic aldehydes, medium-chain aliphatic aldehydes, and aromatic aldehydes, or may be at least one selected from a group consisting of acetaldehyde, malondialdehyde, butanal, 2-methylpropanal, pentanal, 2-methylbutanal, 3-methylbutanal, hexanal, crotonaldehyde, 4-hydroxy-2-hexenal, 4-hydroxy-2-nonenal, 2,4-nonadienal, heptanal, octanal, nonanal, decanal, 2,4-decadienal, and benzaldehyde.

The method for producing a plant-based milk-fermented liquid includes a step of bringing a particular lactic acid bacterium/bacteria into contact with a plant-based milk. The step of bringing a particular lactic acid bacterium/bacteria into contact with a plant-based milk may be a fermentation step of adding the particular lactic acid bacterium/bacteria to the plant-based milk and carrying out lactic acid fermentation. More specifically, by maintaining a plant-based milk at a predetermined fermentation temperature, adding a predetermined amount of a culture liquid of a lactic acid bacterium/bacteria thereto, and then carrying out lactic acid fermentation for a predetermined fermentation time, a desired plant-based milk-fermented liquid may be obtained.

The lactic acid bacterium/bacteria used for the contact with the plant-based milk may be a preculture preliminarily obtained by culturing in an appropriate medium, or may be a frozen product obtained by mixing the preculture with a cryoprotective agent and freezing the resulting mixture, or may be a powder obtained by freeze-drying the preculture. The medium used for the preparation of the preculture may be selected as appropriate from media normally used for culture of lactic acid bacteria. Examples of the medium include MRS Medium (manufactured by BD Japan). Regarding the culture conditions, the culture may be carried out, for example, under static or anaerobic conditions at 30° C. to 40° C. for 12 hours to 32 hours.

The amount of the preculture of the lactic acid bacterium/bacteria added to the plant-based milk may be, for example, 0.1% by volume to 30% by volume, preferably 0.5% by volume to 20% by volume, more preferably 1% by volume to 10% by volume, with respect to the liquid volume of the plant-based milk.

The fermentation temperature and the fermentation time may be appropriately selected in accordance with the culture conditions, the lactic acid bacterial strain(s) added, and the like. The fermentation temperature may be, for example, 10° C. to 45° C., preferably 20° C. to 40° C., more preferably 30° C. to 40° C. The fermentation time may be, for example, 1 hour to 72 hours, preferably 6 hours to 48 hours, more preferably 12 hours to 32 hours.

In the method for producing a plant-based milk-fermented liquid, the aldehyde content in the plant-based milk is reduced by the fermentation step. The residual ratio (%), obtained by dividing the aldehyde content in the resulting plant-based milk-fermented liquid by the aldehyde content in a plant-based milk obtained by the same process except that no lactic acid bacterium is brought into contact, in the case of aromatic aldehydes is, for example, not more than 85%, preferably not more than 70%, more preferably not more than 60%, still more preferably not more than 50%. The lower limit of the residual ratio (%) is not limited, and may be, for example, not less than 1%, or may be preferably not less than 5%. The residual ratio (%) of aldehydes in the case of aliphatic aldehydes is, for example, not more than 55%, preferably not more than 45%, more preferably not more than 40%, still more preferably not more than 35%, still more preferably not more than 30%, or not more than 20%. The lower limit of the residual ratio (%) is not limited, and may be, for example, not less than 0%, preferably not less than 1%, or may be not less than 2%.

The lactic acid bacterium/bacteria contained in the plant-based milk-fermented liquid obtained in the fermentation step may be in the state of viable cells as they are, or may be killed through high-temperature treatment or the like. The high-temperature treatment may be carried out, for example, by treating the resulting plant-based milk-fermented liquid for a predetermined time at a temperature of as high as not less than 63° C.

The plant-based milk-fermented liquid obtained by the production method may be provided as a lactic acid fermented beverage as it is, or the plant-based milk-fermented liquid may be subjected to a predetermined post-treatment to provide a lactic acid fermented beverage or lactic acid fermented food in a desired form. Examples of the post-treatment include a concentration step for making the plant-based milk-fermented liquid into the form of a syrup; a step of adding a desired additive(s) (such as a flavor); a step of mixing with a carbonated beverage, a fruit juice beverage, an alcoholic beverage, or the like; and a food processing step.

Examples of the additives in the post-treatment step include sugar alcohols such as sorbitol, erythritol, maltitol, and xylitol; high-intensity sweeteners such as aspartame, stevioside, sucralose, and acesulfame K; organic acids such as citric acid, tartaric acid, malic acid, succinic acid, and lactic acid; vitamins such as L-ascorbic acid, dl-α-tocopherol, vitamin Bs, nicotinamide, and calcium pantothenate; surfactants such as glycerin fatty acid esters, polyglycerin fatty acid esters, sucrose fatty acid esters, sorbitan fatty acid esters, and propylene glycol fatty acid esters; thickening agents such as gum arabic, carrageenan, pectin, and agar; stabilizers such as casein and gelatin; amino acids; minerals such as calcium salts; additives such as sodium ascorbate, sodium erythorbate, glycerin, and propylene glycol; dyes; flavors; and preservatives.

Examples of the lactic acid fermented beverage obtained by the post-treatment step include carbonated beverages, fruit juice beverages, alcoholic beverages, syrups, and fruit-flavored beverages. To the lactic acid fermented beverage, other beverages such as soy milk may be added as long as the effect of the present invention is not impaired. Examples of the lactic acid fermented food obtained by the post-treatment step include cold confectionery such as jelly, yogurt, pudding, and ice cream; candy; soft candy; gum; and jam.

EXAMPLES

The present invention is described below more concretely by way of Examples. However, the present invention is not limited to these Examples.

Reference Example 1

As lactic acid bacteria, the bacterial strains shown in Table 1 were provided. All bacterial strains provided were type strains. Using a medium prepared by adding 0.05% by mass cysteine hydrochloride to MRS Medium (manufactured by BD Japan), each lactic acid bacterium was cultured in an environment at 37° C. under anaerobic conditions for 16 hours to prepare a preculture of the lactic acid bacterium. Subsequently, 0.05% by mass cysteine hydrochloride and 0.05% by volume acetaldehyde were added to MRS Medium (manufactured by BD Japan), and the preculture of the lactic acid bacterium was added thereto at 5% by volume, followed by performing culture in an environment at 37° C. under anaerobic conditions for 16 hours. Subsequently, the bacterial cells were removed by centrifuging the culture, to obtain a culture supernatant. The concentration of acetaldehyde contained in the culture supernatant was quantified using F-kit Acetaldehyde (manufactured by JK International). The residual ratio (%) of acetaldehyde was calculated by dividing the acetaldehyde concentration in each culture supernatant by the average acetaldehyde concentration in the uninoculated medium, and multiplying the resulting value by 100. The sample data number (n number) was set to 3. The results are shown in Table 1 and FIG. 1.

comparison with the residual ratio in the case of *Lactobacillus brevis* T. A significant difference was assumed at a level of P<0.05. The sample data number (n number) was set to 3.

TABLE 2

| | Residual ratio (%) | | |
| --- | --- | --- | --- |
| Strain name | Average | Standard deviation | p-value (vs. *L. brevis* T) |
| uninoculated medium — | 100.0 | 3.4 | 0.025 |
| *L. gasseri* T JCM1131 | 116.7 | 3.6 | 0.065 |
| *L. fructivorans* T JCM1117 | 107.0 | 1.9 | 0.233 |
| *L. brevis* T JCM1059 | 109.6 | 1.9 | |
| *L. fermentum* T JCM1173 | 1.4 | 0.4 | 0.000 |
| *L. fermentum* CP1299 CP1299 | 0.0 | 0.0 | 0.000 |
| *L. fermentum* CP3024 CP3024 | 0.0 | 0.0 | 0.000 |
| *L. reuteri* T JCM1112 | 0.0 | 0.0 | 0.000 |
| *L. reuteri* CP3017 CP3017 | 0.0 | 0.0 | 0.000 |
| *L. reuteri* CP3019 CP3019 | 0.0 | 0.0 | 0.000 |
| *L. mucosae* T JCM12515 | 0.0 | 0.0 | 0.000 |
| *L. oris* T JCM11028 | 0.0 | 0.0 | 0.000 |

Under the high-concentration conditions, particular bacterial species were found to show higher abilities to reduce the amount of acetaldehyde compared to *Lactobacillus brevis* T. Under the low-concentration conditions, *Lactobacillus fructivorans* T was found to show a high ability to reduce the amount of acetaldehyde similarly to particular bacterial species. However, under the high-concentration conditions, the ability of this species was equivalent to that

TABLE 1

| | Strain name | Average | Standard deviation | | Strain name | Average | Standard deviation |
| --- | --- | --- | --- | --- | --- | --- | --- |
| | | Residual ratio (%) | | | | Residual ratio (%) | |
| uninoculated medium | — | 100.0 | 6.2 | *L. paracasei* T | JCM8130 | 46.8 | 1.9 |
| *L. acidophilus* T | JCM1132 | 40.5 | 4.8 | *L. plantarum* T | JCM1149 | 55.6 | 0.8 |
| *L. amylovorus* T | JCM1126 | 39.3 | 1.5 | *L. reuteri* T | JCM1112 | 0.0 | 0.0 |
| *L. brevis* T | JCM1059 | 0.1 | 0.1 | *L. rhamnosus* T | JCM1136 | 21.0 | 2.2 |
| *L. bulgaricus* T | JCM1002 | 73.6 | 2.2 | *L. salivarius* T | JCM1231 | 27.0 | 3.7 |
| *L. casei* T | JCM1134 | 14.1 | 4.2 | *L. tolerans* T | JCM1171 | 70.9 | 9.2 |
| *L. crispatus* T | JCM1185 | 15.3 | 3.0 | *B. adolescentis* T | JCM1275 | 35.7 | 1.5 |
| *L. delbrueckii* T | JCM1012 | 61.3 | 4.9 | *B. angulatum* T | JCM7096 | 98.2 | 1.5 |
| *L. fermentum* T | JCM1173 | 0.4 | 0.6 | *B. animalis* T | JCM1190 | 40.8 | 9.0 |
| *L. fructivorans* T | JCM1117 | 0.0 | 0.0 | *B. bifidum* T | JCM1255 | 78.7 | 9.6 |
| *L. gallinarum* T | JCM2011 | 40.2 | 3.0 | *B. breve* T | JCM1192 | 26.4 | 0.7 |
| *L. gasseri* T | JCM1131 | 42.6 | 2.7 | *B. catenulatum* T | JCM1194 | 62.5 | 1.5 |
| *L. helveticus* T | JCM1120 | 46.5 | 10.0 | *B. dentium* T | JCM1195 | 31.8 | 0.7 |
| *L. jensenii* T | JCM15953 | 42.0 | 2.2 | *B. gallicum* T | JCM8224 | 82.9 | 4.1 |
| *L. johnsonii* T | JCM2012 | 55.9 | 1.9 | *B. infantis* T | JCM1222 | 65.2 | 0.7 |
| *L. kefirgranum* T | JCM8572 | 49.5 | 2.1 | *B. longum* T | JCM1217 | 50.2 | 2.1 |
| *L. lactis* T | JCM1248 | 55.6 | 5.5 | *B. pseudocatenulatum* T | JCM1200 | 10.2 | 1.5 |
| *L. mali* T | JCM1116 | 0.4 | 0.6 | *B. pseudolongum* T | JCM1205 | 73.3 | 3.9 |
| *L. mucosae* T | JCM12515 | 0.0 | 0.0 | *B. suis* T | JCM1269 | 61.3 | 2.4 |
| *L. oris* T | JCM11028 | 0.0 | 0.0 | *B. thermophilum* T | JCM1207 | 48.0 | 2.7 |

It can be seen that the ability to reduce the amount of acetaldehyde varies among the lactic acid bacterial species.

Reference Example 2

Figure 2:
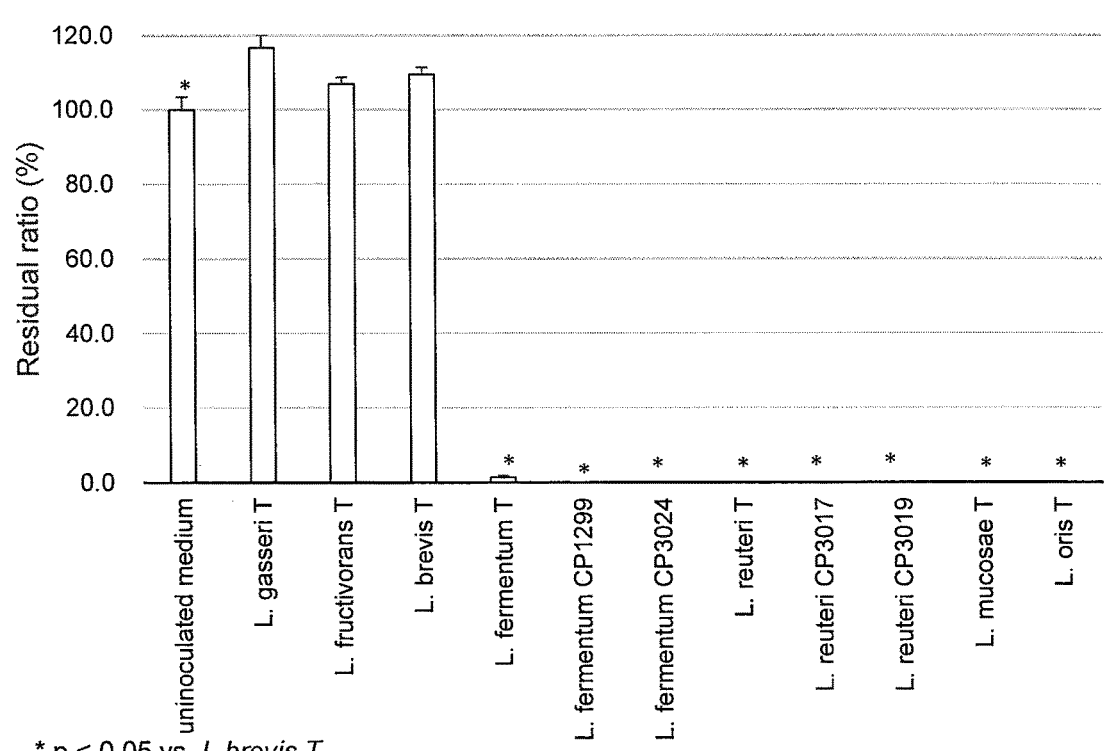
FIG. 2 is a graph showing the abilities of lactic acid bacteria to reduce the amount of acetaldehyde at high concentration.

The ability of each lactic acid bacterium to reduce the amount of acetaldehyde was evaluated in the same manner as in Reference Example 1 except that the bacterial strains shown in Table 2 were used, and that the concentration of the acetaldehyde added was 0.2% by volume. The results are shown in Table 2 and FIG. 2. For statistical processing, the Student t-test was used. The test was carried out based on of *Lactobacillus brevis* T. It can thus be seen that the ability to reduce the amount of acetaldehyde varies among the bacterial species and bacterial strains.

Reference Example 3

Figure 3:
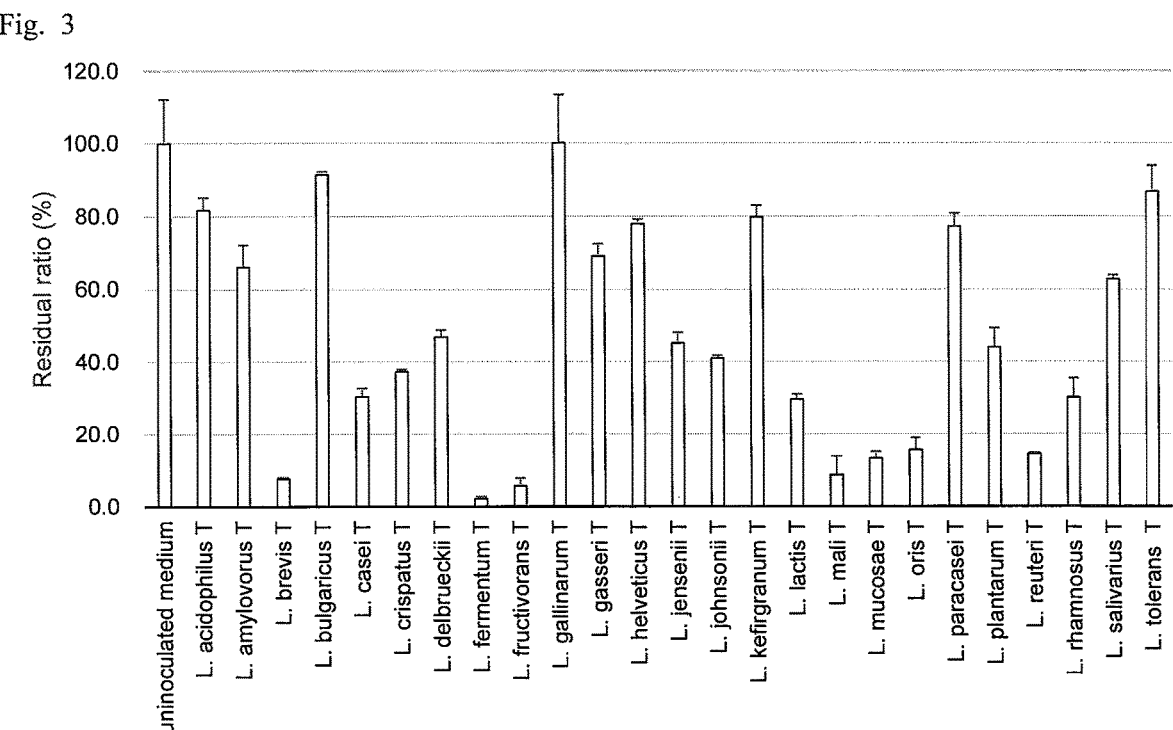
FIG. 3 is a graph showing the abilities of lactic acid bacteria to reduce the amount of hexanal at low concentration.

As lactic acid bacteria, the bacterial strains shown in Table 3 were provided. All strains provided were type strains. Using a medium prepared by adding 0.05% by mass cysteine hydrochloride to MRS Medium (manufactured by BD Japan), each lactic acid bacterium was cultured in an environment at 37° C. under anaerobic conditions for 16 hours to prepare a preculture of the lactic acid bacterium. Subsequently, 0.05% by mass cysteine hydrochloride and 0.05% by volume hexanal were added to MRS Medium (manufactured by BD Japan), and the preculture of the lactic acid bacterium was added thereto at 5% by volume, followed by performing culture in an environment at 37° C. under anaerobic conditions for 16 hours. Subsequently, the bacterial cells were removed by centrifuging the culture, to obtain a culture supernatant. The concentration of hexanal contained in the culture supernatant was quantified by a modification of the LC-MS/MS method described in Drug Test. Analysis, 8, 458-464 (2016). Details of the quantification method are described later. The residual ratio (%) of hexanal was calculated by dividing the hexanal concentration in each culture supernatant by the average hexanal concentration in the uninoculated medium, and multiplying the resulting value by 100. The sample data number (n number) was set to 3. The results are shown in Table 3 and FIG. 3.

TABLE 3

| | | Residual ratio (%) | |
| --- | --- | --- | --- |
| | Strain name | Average | Standard deviation |
| uninoculated medium | — | 100.0 | 12.1 |
| L. acidophilus T | JCM1132 | 81.6 | 3.5 |
| L. amylovorus T | JCM1126 | 66.1 | 5.9 |
| L. brevis T | JCM1059 | 7.7 | 0.4 |
| L. bulgaricus T | JCM1002 | 91.4 | 0.9 |
| L. casei T | JCM1134 | 30.3 | 2.3 |
| L. crispatus T | JCM1185 | 37.4 | 0.6 |
| L. delbrueckii T | JCM1012 | 46.9 | 1.8 |
| L. fermentum T | JCM1173 | 2.2 | 0.6 |
| L. fructivorans T | JCM1117 | 5.8 | 2.1 |
| L. gallinarum T | JCM2011 | 100.2 | 13.2 |
| L. gasseri T | JCM1131 | 69.0 | 3.5 |
| L. helveticus T | JCM1120 | 77.9 | 1.2 |
| L. jensenii T | JCM15953 | 45.2 | 2.9 |
| L. johnsonii T | JCM2012 | 41.0 | 0.7 |
| L. kefirgranum T | JCM8572 | 79.8 | 3.1 |
| L. lactis T | JCM1248 | 29.5 | 1.4 |
| L. mali T | JCM1116 | 8.7 | 5.1 |
| L. mucosae T | JCM12515 | 13.3 | 1.8 |
| L. oris T | JCM11028 | 15.5 | 3.4 |
| L. paracasei T | JCM8130 | 77.2 | 3.5 |
| L. plantarum T | JCM1149 | 44.0 | 5.3 |
| L. reuteri T | JCM1112 | 14.5 | 0.3 |
| L. rhamnosus T | JCM1136 | 30.0 | 5.4 |
| L. salivarius T | JCM1231 | 62.7 | 1.2 |
| L. tolerans T | JCM1171 | 86.8 | 7.1 |

It could be confirmed that the ability to reduce the amount of hexanal varies among the lactic acid bacterial species.

Reference Example 4

Figure 4:
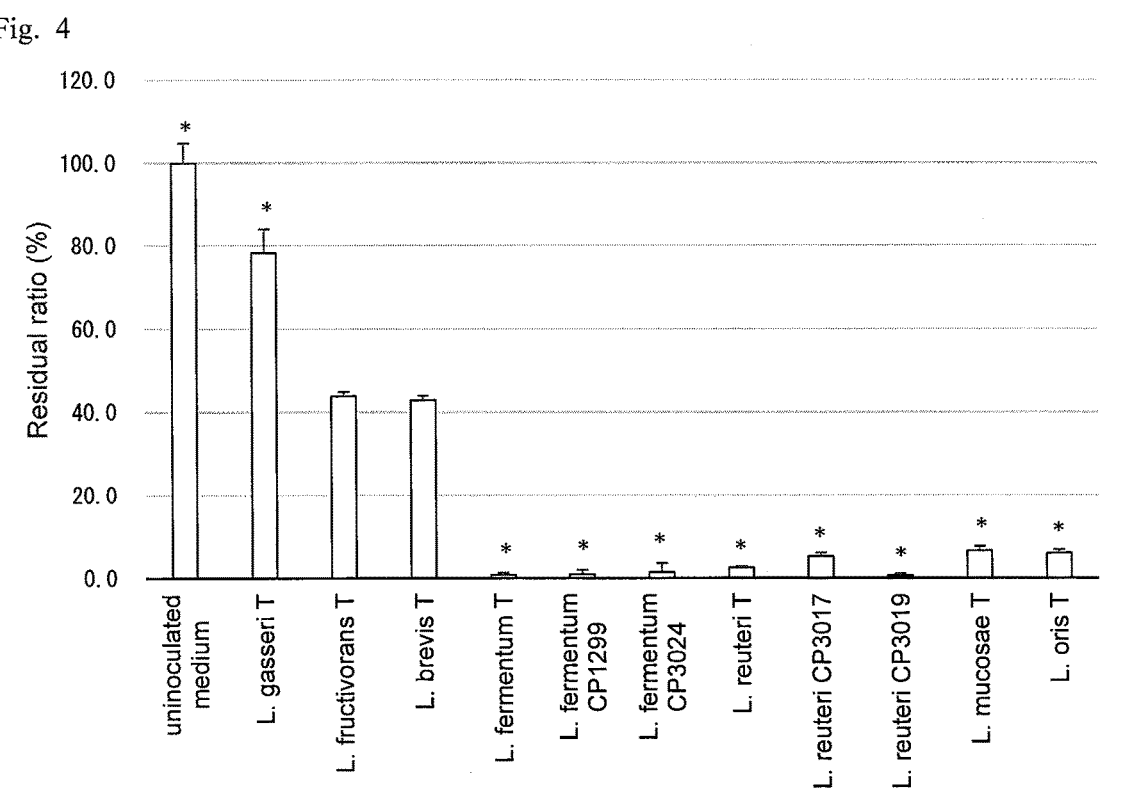
FIG. 4 is a graph showing the abilities of lactic acid bacteria to reduce the amount of hexanal at high concentration.

The ability of each lactic acid bacterium to reduce the amount of hexanal was evaluated in the same manner as in Reference Example 3 except that the bacterial strains shown in Table 4 were used, and that the concentration of the hexanal added was 0.2% by volume. The results are shown in Table 4 and FIG. 4. For statistical processing, the Student t-test was used. The test was carried out based on comparison with the residual ratio in the case of *Lactobacillus brevis* T. A significant difference was assumed at a level of P<0.05. The sample data number (n number) was set to 3.

TABLE 4

| | | Residual ratio (%) | | |
| --- | --- | --- | --- | --- |
| | Strain name | Average | Standard deviation | p-value (vs. L. brevis T) |
| uninoculated medium | — | 100.0 | 4.8 | 0.000 |
| L. gasseri T | JCM1131 | 78.3 | 5.7 | 0.001 |
| L. fructivorans T | JCM1117 | 43.8 | 1.1 | 0.420 |
| L. brevis T | JCM1059 | 42.9 | 1.0 | |
| L. fermentum T | JCM1173 | 0.8 | 0.5 | 0.000 |
| L. fermentum CP1299 | CP1299 | 1.0 | 1.0 | 0.000 |
| L. fermentum CP3024 | CP3024 | 1.5 | 2.1 | 0.000 |
| L. reuteri T | JCM1112 | 2.6 | 0.2 | 0.000 |
| L. reuteri CP3017 | CP3017 | 5.2 | 0.8 | 0.000 |
| L. reuteri CP3019 | CP3019 | 0.6 | 0.5 | 0.000 |
| L. mucosae T | JCM12515 | 6.5 | 1.1 | 0.000 |
| L. oris T | JCM11028 | 5.9 | 0.9 | 0.000 |

Under the high-concentration conditions, particular bacterial species were found to show higher abilities to reduce the amount of hexanal compared to *Lactobacillus brevis* T. Under the low-concentration conditions, *Lactobacillus fructivorans* T was found to show a high ability to reduce the amount of hexanal similarly to particular bacterial species. However, under the high-concentration conditions, the ability of this species to reduce the amount of hexanal was equivalent to that of *Lactobacillus brevis* T. It can thus be seen that the ability to reduce the amount of hexanal varies among the bacterial species and bacterial strains.

Reference Example 5

Figure 5:
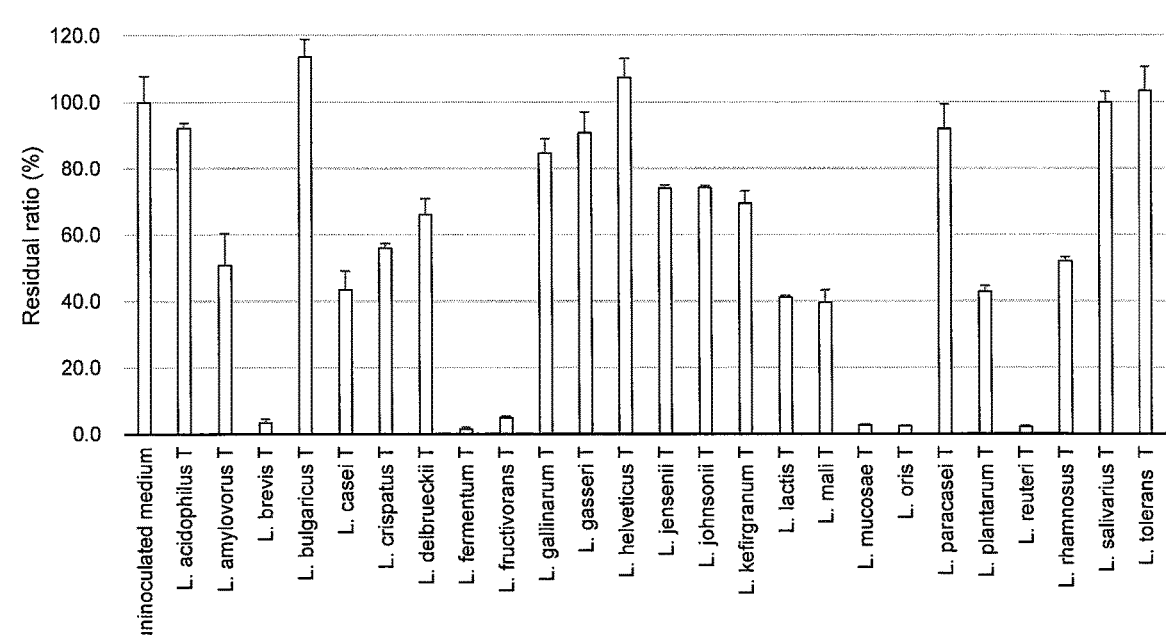
FIG. 5 is a graph showing the abilities of lactic acid bacteria to reduce the amount of benzaldehyde at low concentration.

As lactic acid bacteria, the bacterial strains shown in Table 5 were provided. All strains provided were type strains. Using a medium prepared by adding 0.05% by mass cysteine hydrochloride to MRS Medium (manufactured by BD Japan), each lactic acid bacterium was cultured in an environment at 37° C. under anaerobic conditions for 16 hours to prepare a preculture of the lactic acid bacterium. Subsequently, 0.05% by mass cysteine hydrochloride and 0.05% by volume benzaldehyde were added to MRS Medium (manufactured by BD Japan), and the preculture of the lactic acid bacterium was added thereto at 5% by volume, followed by performing culture in an environment at 37° C. under anaerobic conditions for 16 hours. Subsequently, the bacterial cells were removed by centrifuging the culture, to obtain a culture supernatant. The concentration of benzaldehyde contained in the culture supernatant was quantified by a modification of the LC-MS/MS method described in Drug Test. Analysis, 8, 458-464 (2016). Details of the quantification method are described later. The residual ratio (%) of benzaldehyde was calculated by dividing the benzaldehyde concentration in each culture supernatant by the average benzaldehyde concentration in the uninoculated medium, and multiplying the resulting value by 100. The sample data number (n number) was set to 3. The results are shown in Table 5 and FIG. 5.

TABLE 5

| | | Residual ratio (%) | |
| --- | --- | --- | --- |
| | Strain name | Average | Standard deviation |
| uninoculated medium | — | 100.0 | 7.8 |
| L. acidophilus T | JCM1132 | 92.3 | 1.6 |
| L. amylovorus T | JCM1126 | 50.8 | 9.5 |

US 12,616,220 B2

13

TABLE 5-continued

| | | Residual ratio (%) | |
| Strain name | | Average | Standard deviation |
|---|---|---|---|
| L. brevis T | JCM1059 | 3.3 | 1.3 |
| L. bulgaricus T | JCM1002 | 113.5 | 5.3 |
| L. casei T | JCM1134 | 43.5 | 5.7 |
| L. crispatus T | JCM1185 | 56.0 | 1.3 |
| L. delbrueckii T | JCM1012 | 66.0 | 4.8 |
| L. fermentum T | JCM1173 | 1.5 | 0.6 |
| L. fructivorans T | JCM1117 | 4.9 | 0.5 |
| L. gallinarum T | JCM2011 | 84.7 | 4.4 |
| L. gasseri T | JCM1131 | 90.8 | 6.1 |
| L. helveticus T | JCM1120 | 107.4 | 5.7 |
| L. jensenii T | JCM15953 | 74.0 | 1.0 |
| L. johnsonii T | JCM2012 | 74.1 | 0.6 |
| L. kefirgranum T | JCM8572 | 69.5 | 3.7 |
| L. lactis T | JCM1248 | 41.1 | 0.5 |
| L. mali T | JCM1116 | 39.6 | 3.6 |
| L. mucosae T | JCM12515 | 2.6 | 0.3 |
| L. oris T | JCM11028 | 2.5 | 0.2 |
| L. paracasei T | JCM8130 | 92.0 | 7.3 |
| L. plantarum T | JCM1149 | 42.9 | 1.6 |
| L. reuteri T | JCM1112 | 2.1 | 0.3 |
| L. rhamnosus T | JCM1136 | 52.0 | 1.2 |
| L. salivarius T | JCM1231 | 100.0 | 3.1 |
| L. tolerans T | JCM1171 | 103.4 | 7.2 |

It could be confirmed that the ability to reduce the amount of benzaldehyde varies among the lactic acid bacterial species.

Reference Example 6

Figure 6:
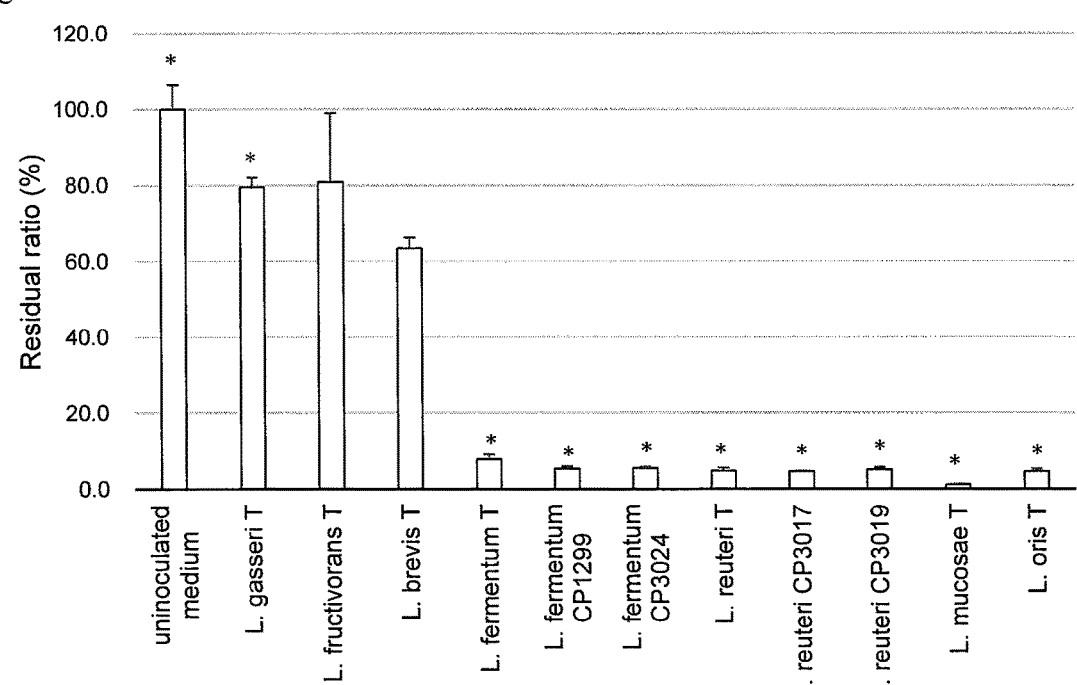
FIG. 6 is a graph showing the abilities of lactic acid bacteria to reduce the amount of benzaldehyde at high concentration.
Figure 7:
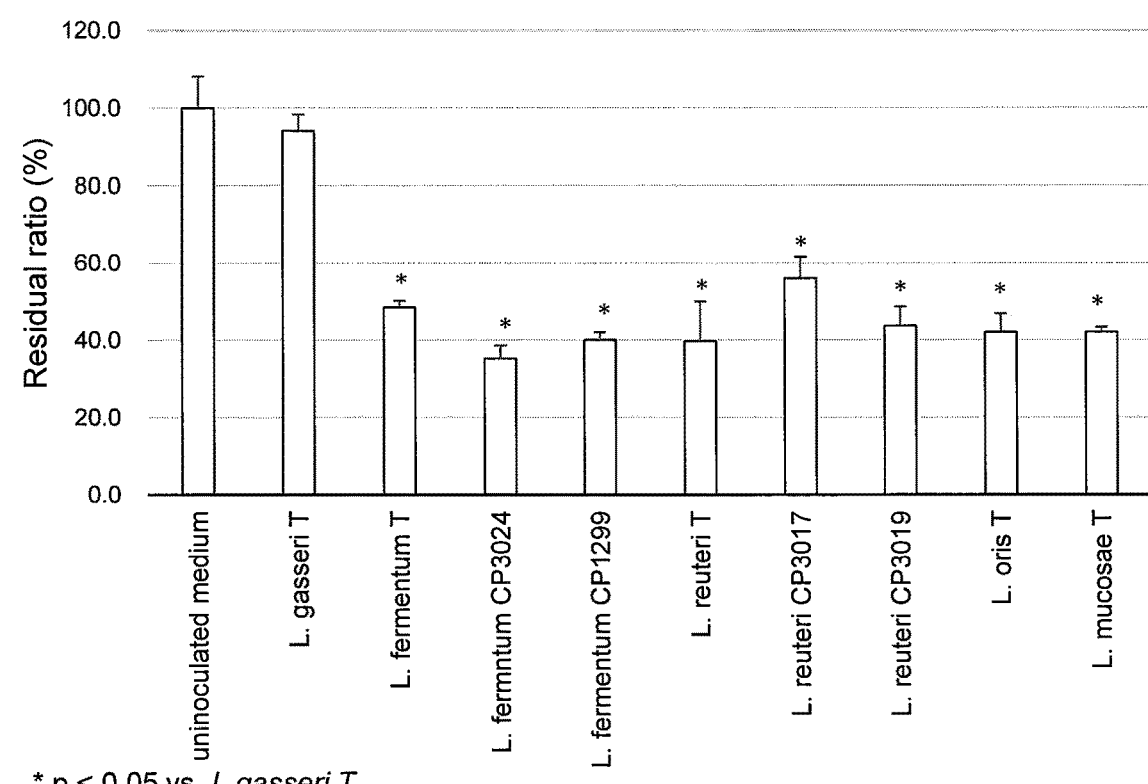
FIG. 7 is a graph showing the abilities of lactic acid bacteria to reduce the amount of benzaldehyde contained in a plant-based milk derived from brown rice.
Figure 8:
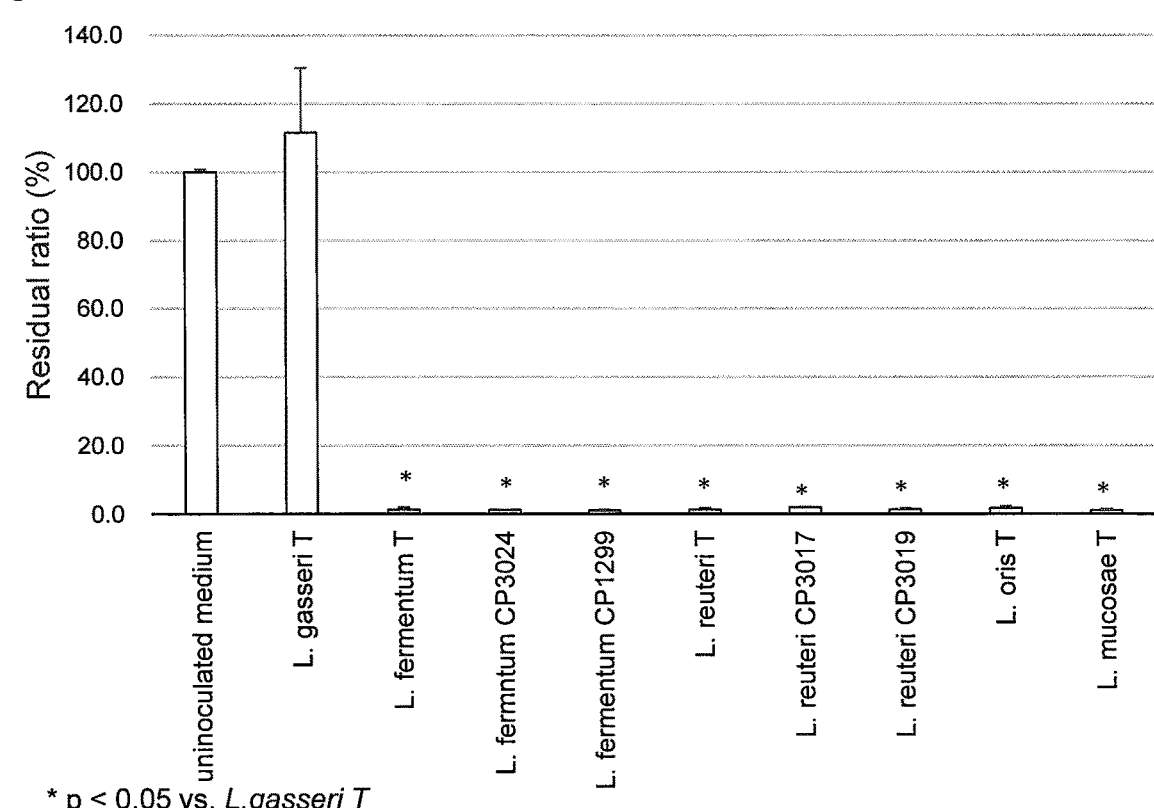
FIG. 8 is a graph showing the abilities of lactic acid bacteria to reduce the amount of 2,4-decadienal contained in a plant-based milk derived from brown rice.
Figure 9:
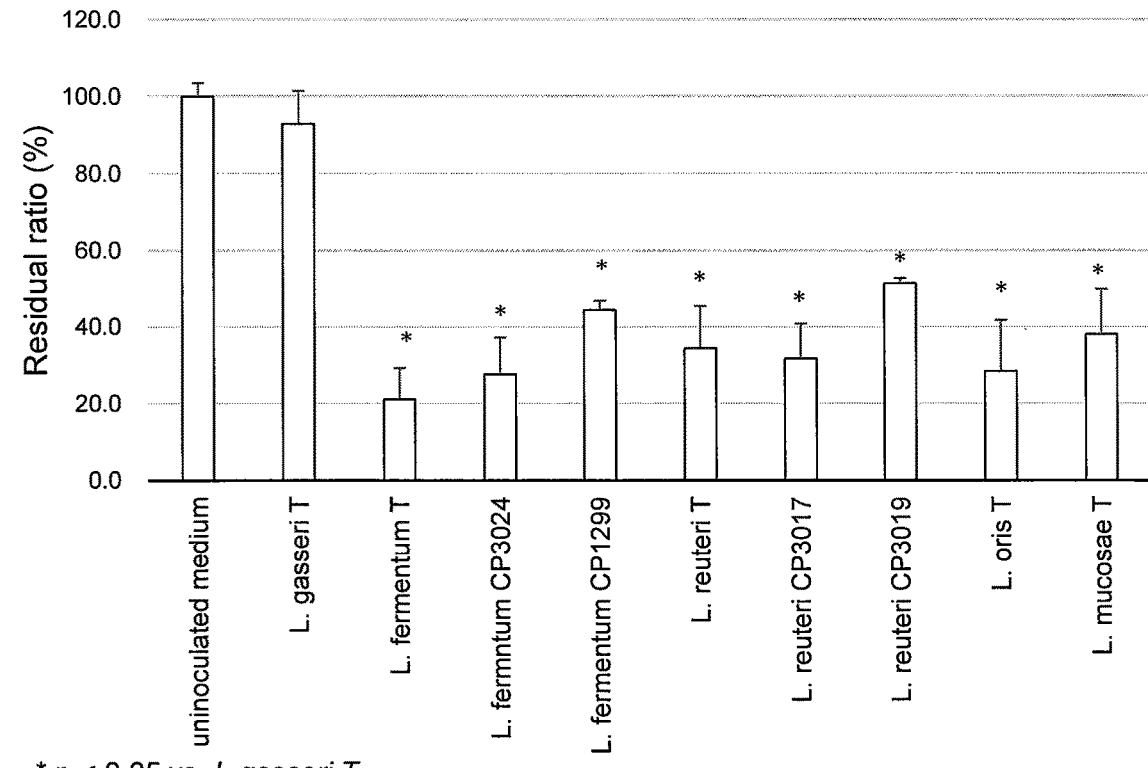
FIG. 9 is a graph showing the abilities of lactic acid bacteria to reduce the amount of 2-methylbutanal contained in a plant-based milk derived from brown rice.
Figure 10:
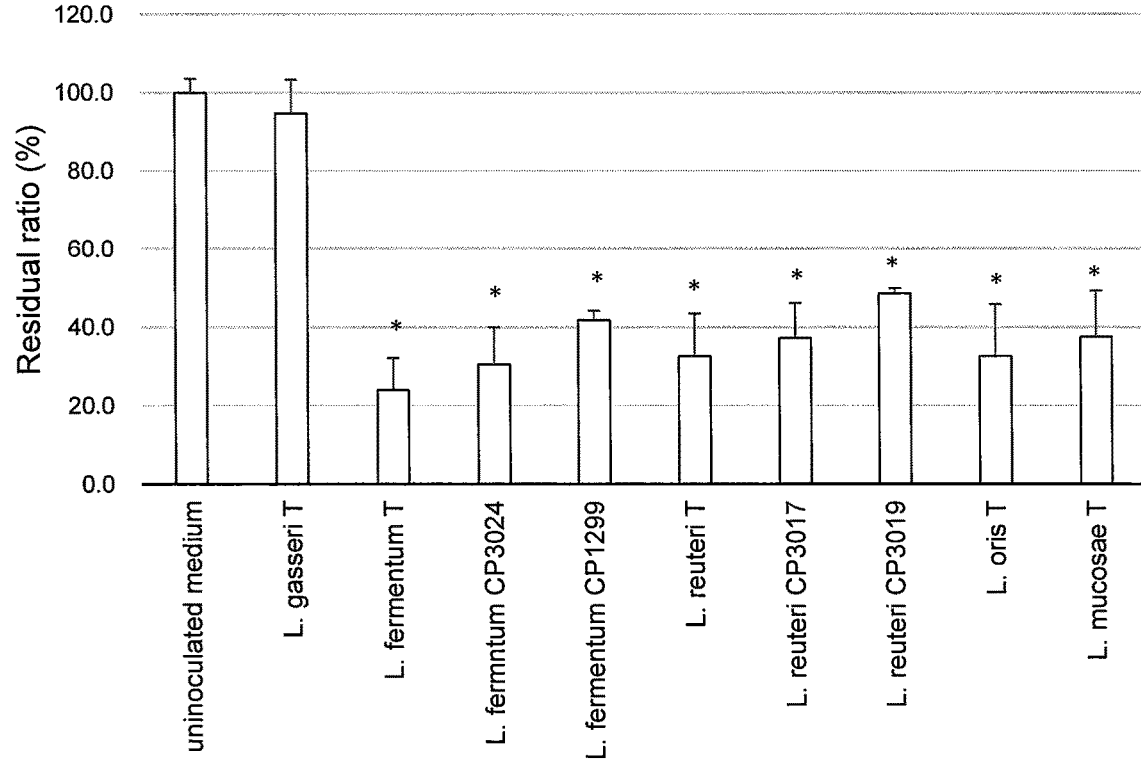
FIG. 10 is a graph showing the abilities of lactic acid bacteria to reduce the amount of 2-methylpropanal contained in a plant-based milk derived from brown rice.
Figure 11:
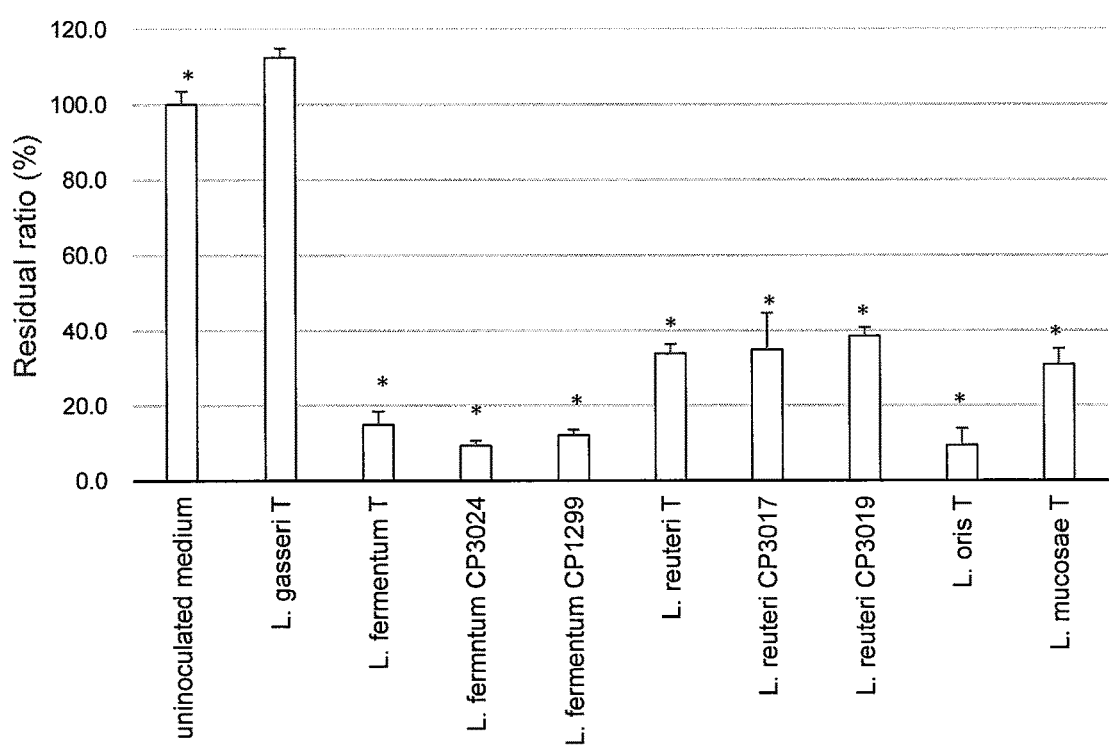
FIG. 11 is a graph showing the abilities of lactic acid bacteria to reduce the amount of 3-methylbutanal contained in a plant-based milk derived from brown rice.
Figure 12:
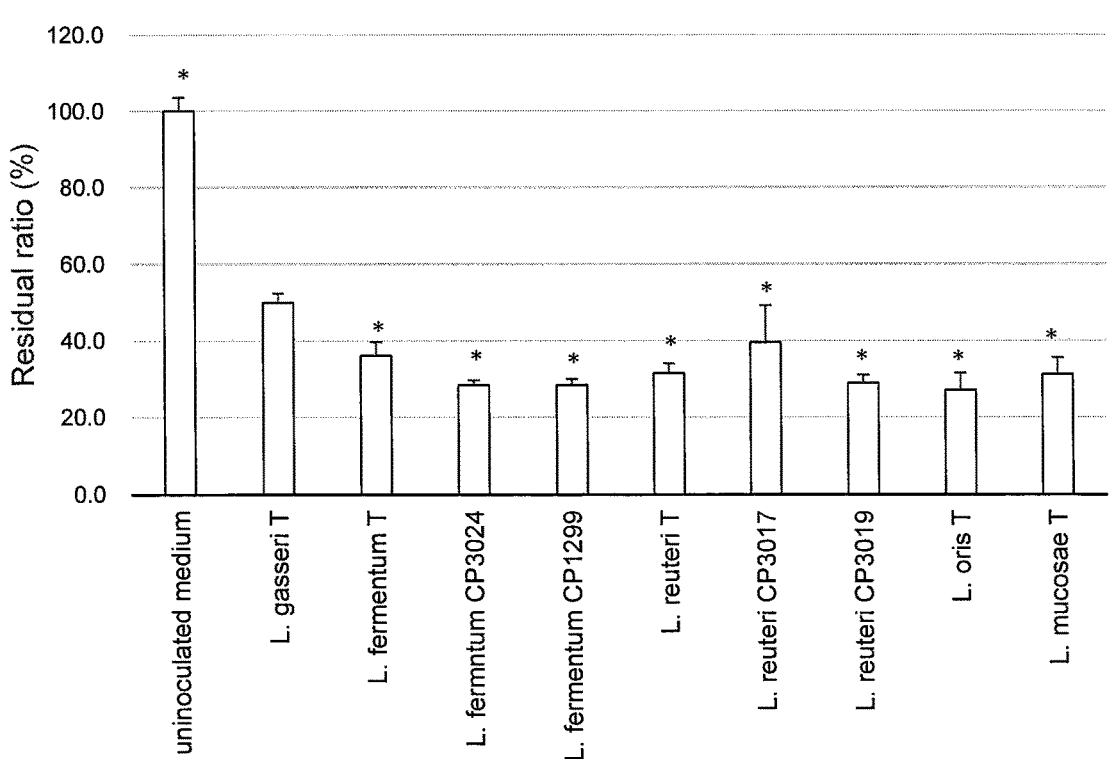
FIG. 12 is a graph showing the abilities of lactic acid bacteria to reduce the amount of hexanal contained in a plant-based milk derived from brown rice.

The ability of each lactic acid bacterium to reduce the amount of benzaldehyde was evaluated in the same manner as in Reference Example 5 except that the bacterial strains shown in Table 6 were used, and that the concentration of the benzaldehyde added was 0.2% by volume. The results are shown in Table 6 and FIG. 6. For statistical processing, the Student t-test was used. The test was carried out based on comparison with the residual ratio in the case of *Lactobacillus brevis* T. A significant difference was assumed at a level of P<0.05. The sample data number (n number) was set to 3.

TABLE 6

| | | Residual ratio (%) | | |
| Strain name | | Average | Standard deviation | p-value (vs. L. brevis T) |
|---|---|---|---|---|
| uninoculated medium | — | 100.0 | 6.5 | 0.002 |
| L. gasseri T | JCM1131 | 79.4 | 2.6 | 0.004 |
| L. fructivorans T | JCM1117 | 80.8 | 18.1 | 0.249 |
| L. brevis T | JCM1059 | 63.4 | 2.9 | |
| L. fermentum T | JCM1173 | 7.8 | 1.3 | 0.000 |
| L. fermentum CP1299 | CP1299 | 5.5 | 0.6 | 0.000 |
| L. fermentum CP3024 | CP3024 | 5.6 | 0.2 | 0.000 |
| L. reuteri T | JCM1112 | 4.8 | 0.8 | 0.000 |
| L. reuteri CP3017 | CP3017 | 4.7 | 0.1 | 0.000 |
| L. reuteri CP3019 | CP3019 | 5.2 | 0.6 | 0.000 |
| L. mucosae T | JCM12515 | 1.1 | 0.1 | 0.000 |
| L. oris T | JCM11028 | 4.7 | 0.6 | 0.000 |

Under the high-concentration conditions, particular bacterial species were found to show higher benzaldehyde-reducing abilities compared to *Lactobacillus brevis* T. Under the low-concentration conditions, *Lactobacillus fructivorans* T was found to show a high ability to reduce the amount of benzaldehyde similarly to particular bacterial species. However, under the high-concentration conditions, the ability of this species to reduce the amount of benzaldehyde was equivalent to that of *Lactobacillus brevis* T. It can thus be seen that the ability to reduce the amount of benzaldehyde varies among the bacterial species and bacterial strains.

Example 1

As lactic acid bacteria, the bacterial strains shown in Table 7 to Table 12 were provided. Using MRS Medium (manufactured by BD Japan) supplemented with 0.05% by mass cysteine hydrochloride, each lactic acid bacterium was cultured in an environment at 37° C. under anaerobic conditions for 16 hours, to prepare a preculture of each lactic acid bacterial strain. Concentrated rice milk (manufactured by Kikkoman Corporation; raw material: processed brown rice) was diluted 1.67 times with pure water, and sterilized at 95° C. for 15 minutes, to obtain a brown rice milk medium. To the brown rice milk medium, the preculture of the lactic acid bacterium was added at 5% by volume, and static culture was performed in an environment at 37° C. for 16 hours, to obtain a culture as a plant-based milk-fermented liquid. The concentration of each of benzaldehyde, 2,4-decadienal, 2-methylbutanal, 2-methylpropanal, 3-methylbutanal, and hexanal in the obtained culture was quantified by a modification of the LC-MS/MS method described in Drug Test. Analysis, 8, 458-464 (2016). Details of the quantification method are described later. The residual ratio (%) of each aldehyde was calculated by dividing the concentration of the aldehyde in each culture by the average of the concentration of the aldehyde in the uninoculated medium, and multiplying the resulting value by 100. The results are shown in Table 7 to Table 12, and FIG. 7 to FIG. 12. For statistical processing, the Student t-test was used. The test was carried out based on comparison with the residual ratio in the case of *Lactobacillus gasseri* T. The sample data number (n number) was set to 3. A significant difference was assumed at a level of P<0.05.

TABLE 7

| | | Residual ratio (%) | | |
| Benzaldehyde | Strain name | Average | Standard deviation | p-value (vs. L. gasseri T) |
|---|---|---|---|---|
| uninoculated medium | — | 100.0 | 8.1 | 0.413 |
| L. gasseri T | JCM1131 | 94.1 | 4.2 | |
| L. fermentum T | JCM1173 | 48.4 | 1.7 | 0.000 |
| L. fermntum CP3024 | CP3024 | 35.2 | 3.4 | 0.000 |
| L. fermentum CP1299 | CP1299 | 40.0 | 2.0 | 0.000 |
| L. reuteri T | JCM1112 | 39.6 | 10.2 | 0.002 |
| L. reuteri CP3017 | CP3017 | 56.0 | 5.7 | 0.002 |
| L. reuteri CP3019 | CP3019 | 43.6 | 4.9 | 0.000 |
| L. oris T | JCM11028 | 42.0 | 4.7 | 0.000 |
| L. mucosae T | JCM12515 | 42.1 | 1.3 | 0.000 |

TABLE 8

| | | Residual ratio (%) | | |
| 2,4-Decadienal | Strain name | Average | Standard deviation | p-value (vs. L. gasseri T) |
|---|---|---|---|---|
| uninoculated medium | — | 100.0 | 0.8 | 0.438 |
| L. gasseri T | JCM1131 | 111.5 | 18.8 | |
| L. fermentum T | JCM1173 | 1.3 | 0.7 | 0.001 |

TABLE 8-continued

| 2,4-Decadienal | Strain name | Residual ratio (%) | | |
| --- | --- | --- | --- | --- |
| | | Average | Standard deviation | p-value (vs. *L. gasseri* T) |
| *L. fermntum* CP3024 | CP3024 | 1.2 | 0.0 | 0.001 |
| *L. fermentum* CP1299 | CP1299 | 1.0 | 0.3 | 0.001 |
| *L. reuteri* T | JCM1112 | 1.3 | 0.5 | 0.001 |
| *L. reuteri* CP3017 | CP3017 | 1.9 | 0.1 | 0.001 |
| *L. reuteri* CP3019 | CP3019 | 1.3 | 0.3 | 0.001 |
| *L. oris* T | JCM11028 | 1.7 | 0.6 | 0.001 |
| *L. mucosae* T | JCM12515 | 1.0 | 0.4 | 0.001 |

TABLE 9

| 2-Methylbutanal | Strain name | Residual ratio (%) | | |
| --- | --- | --- | --- | --- |
| | | Average | Standard deviation | p-value (vs. *L. gasseri* T) |
| uninoculated medium | — | 100.0 | 3.5 | 0.340 |
| *L. gasseri* T | JCM1131 | 92.9 | 8.5 | |
| *L. fermentum* T | JCM1173 | 21.1 | 8.2 | 0.001 |
| *L. fermntum* CP3024 | CP3024 | 27.6 | 9.6 | 0.002 |
| *L. fermentum* CP1299 | CP1299 | 44.4 | 2.4 | 0.002 |
| *L. reuteri* T | JCM1112 | 34.4 | 11.0 | 0.004 |
| *L. reuteri* CP3017 | CP3017 | 31.7 | 9.1 | 0.002 |
| *L. reuteri* CP3019 | CP3019 | 51.3 | 1.3 | 0.002 |
| *L. oris* T | JCM11028 | 28.4 | 13.4 | 0.005 |
| *L. mucosae* T | JCM12515 | 38.0 | 11.8 | 0.006 |

TABLE 10

| 2-Methylpropanal | Strain name | Residual ratio (%) | | |
| --- | --- | --- | --- | --- |
| | | Average | Standard deviation | p-value (vs. *L. gasseri* T) |
| uninoculated medium | — | 100.0 | 5.7 | 0.276 |
| *L. gasseri* T | JCM1131 | 94.7 | 1.6 | |
| *L. fermentum* T | JCM1173 | 23.9 | 4.8 | 0.000 |
| *L. fermntum* CP3024 | CP3024 | 30.4 | 7.4 | 0.000 |
| *L. fermentum* CP1299 | CP1299 | 41.8 | 1.4 | 0.000 |
| *L. reuteri* T | JCM1112 | 32.5 | 5.5 | 0.000 |
| *L. reuteri* CP3017 | CP3017 | 37.1 | 7.3 | 0.000 |
| *L. reuteri* CP3019 | CP3019 | 48.6 | 0.9 | 0.000 |
| *L. oris* T | JCM11028 | 32.5 | 12.6 | 0.002 |
| *L. mucosae* T | JCM12515 | 37.5 | 8.5 | 0.001 |

TABLE 11

| 3-Metylbutanal | Strain name | Residual ratio (%) | | |
| --- | --- | --- | --- | --- |
| | | Average | Standard deviation | p-value (vs. *L. gasseri* T) |
| uninoculated medium | — | 100.0 | 3.5 | 0.015 |
| *L. gasseri* T | JCM1131 | 112.4 | 2.4 | |
| *L. fermentum* T | JCM1173 | 14.9 | 3.6 | 0.000 |
| *L. fermntum* CP3024 | CP3024 | 9.3 | 1.4 | 0.000 |
| *L. fermentum* CP1299 | CP1299 | 12.1 | 1.5 | 0.000 |
| *L. reuteri* T | JCM1112 | 33.9 | 2.5 | 0.000 |
| *L. reuteri* CP3017 | CP3017 | 34.9 | 9.7 | 0.000 |
| *L. reuteri* CP3019 | CP3019 | 38.6 | 2.2 | 0.000 |
| *L. oris* T | JCM11028 | 9.4 | 4.5 | 0.000 |
| *L. mucosae* T | JCM12515 | 30.9 | 4.3 | 0.000 |

TABLE 12

| Hexanal | Strain name | Residual ratio (%) | | |
| --- | --- | --- | --- | --- |
| | | Average | Standard deviation | p-value (vs. *L. gasseri* T) |
| uninoculated medium | — | 100.0 | 2.4 | 0.000 |
| *L. gasseri* T | JCM1131 | 50.0 | 2.1 | |
| *L. fermentum* T | JCM1173 | 36.0 | 3.0 | 0.006 |
| *L. fermntum* CP3024 | CP3024 | 28.3 | 2.3 | 0.001 |
| *L. fermentum* CP1299 | CP1299 | 28.4 | 1.8 | 0.000 |
| *L. reuteri* T | JCM1112 | 31.5 | 5.3 | 0.010 |
| *L. reuteri* CP3017 | CP3017 | 39.6 | 2.4 | 0.010 |
| *L. reuteri* CP3019 | CP3019 | 28.9 | 2.1 | 0.001 |
| *L. oris* T | JCM11028 | 27.1 | 7.5 | 0.015 |
| *L. mucosae* T | JCM12515 | 31.2 | 1.3 | 0.000 |

It could be confirmed that the amounts of aldehydes were significantly reduced by particular bacterial strains compared to the case of the control, *Lactobacillus gasseri* T.

Example 2

Figure 13:
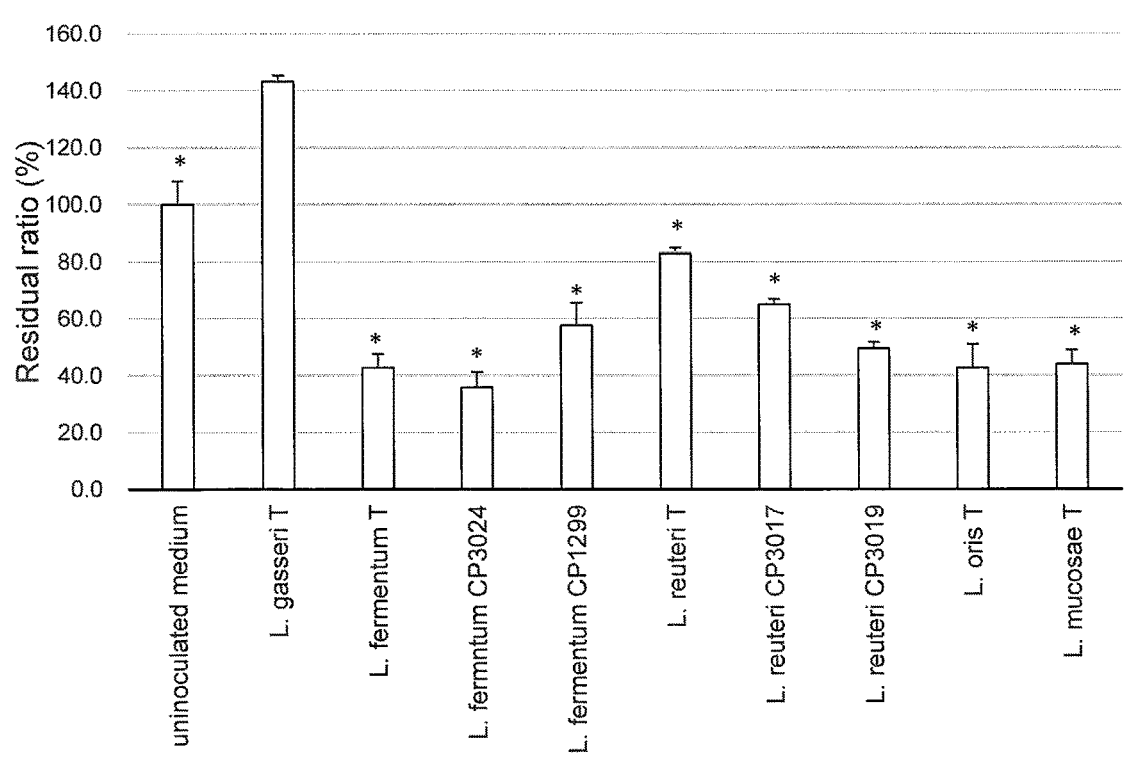
FIG. 13 is a graph showing the abilities of lactic acid bacteria to reduce the amount of benzaldehyde contained in a plant-based milk derived from white rice.
Figure 14:
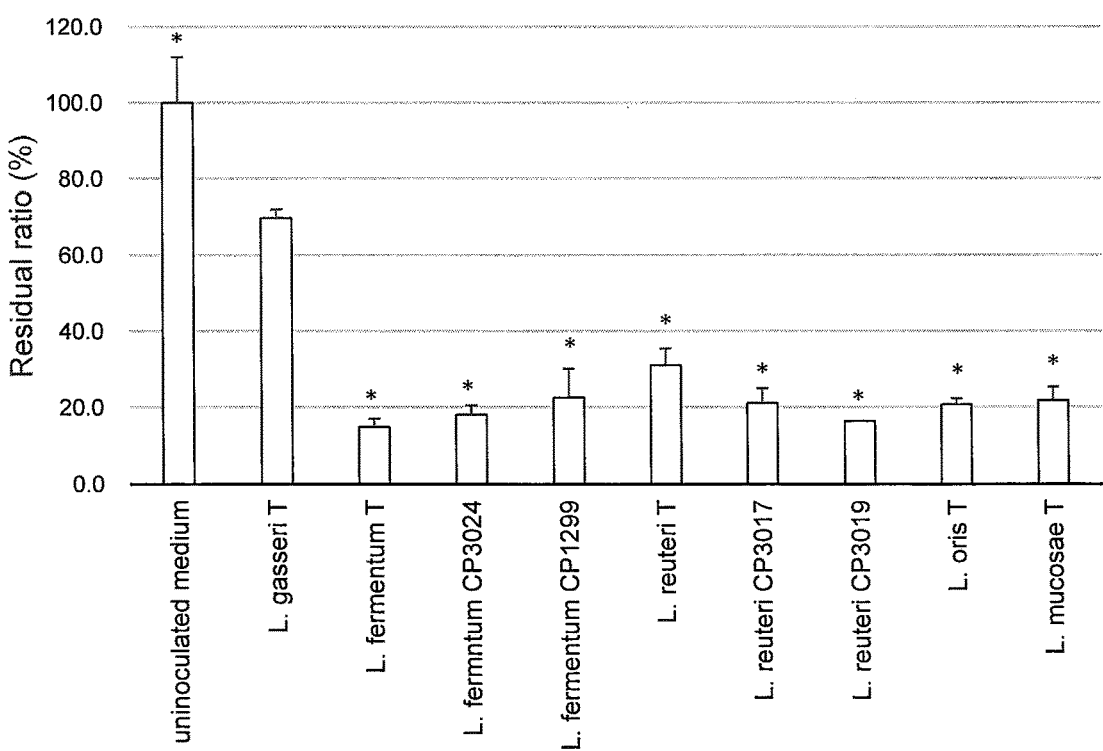
FIG. 14 is a graph showing the abilities of lactic acid bacteria to reduce the amount of hexanal contained in a plant-based milk derived from white rice.

As lactic acid bacteria, the bacterial strains shown in Table 13 and Table 14 were provided. Using MRS Medium (manufactured by BD Japan) supplemented with 0.05% by mass cysteine hydrochloride, each lactic acid bacterium was cultured in an environment at 37° C. under anaerobic conditions for 16 hours, to prepare a preculture of each lactic acid bacterial strain. A commercially available confectionery rice flour (Tomizawa Shoten; material: non-glutinous rice) and pure water were mixed together at a weight ratio of 3:7, and amylase (manufactured by Novozymes, BAN480L) was added thereto at 0.03% by volume. Thereafter, the mixture was allowed to react at 60° C. for 6 hours, and then stirred, followed by sterilization at 95° C. for 15 minutes to provide a white-rice milk medium. To the white-rice milk medium, the preculture of the lactic acid bacterium was added at 5% by volume, and static culture was performed in an environment at 37° C. for 16 hours, to obtain a culture as a plant-based milk-fermented liquid. The concentration of each of benzaldehyde and hexanal contained in the resulting culture was quantified by a modification of the LC-MS/MS method described in Drug Test. Analysis, 8, 458-464 (2016). Details of the quantification method are described later. The residual ratio (%) of each aldehyde was calculated by dividing the concentration of the aldehyde in each culture by the average of the concentration of the aldehyde in the uninoculated medium, and multiplying the resulting value by 100. The results are shown in Table 13 and Table 14, and FIG. 13 and FIG. 14. For statistical processing, the Student t-test was used. The test was carried out based on comparison with the residual ratio in the case of *Lactobacillus gasseri* T. The sample data number (n number) was set to 3. A significant difference was assumed at a level of $P<0.05$.

TABLE 13

| Bezaldehyde | Strain name | Residual ratio (%) | | |
| --- | --- | --- | --- | --- |
| | | Average | Standard deviation | p-value (vs. *L. gasseri* T) |
| uninoculated medium | — | 100.0 | 8.1 | 0.002 |
| *L. gasseri* T | JCM1131 | 143.1 | 2.3 | |
| *L. fermentum* T | JCM1173 | 42.7 | 4.8 | 0.000 |
| *L. fermntum* CP3024 | CP3024 | 35.8 | 5.4 | 0.000 |
| *L. fermentum* CP1299 | CP1299 | 57.5 | 8.1 | 0.000 |

TABLE 13-continued

| Bezaldehyde | Strain name | Residual ratio (%) | | |
| | | Average | Standard deviation | p-value (vs. L. gasseri T) |
| --- | --- | --- | --- | --- |
| *L. reuteri* T | JCM1112 | 82.9 | 2.0 | 0.000 |
| *L. reuteri* CP3017 | CP3017 | 65.1 | 1.9 | 0.000 |
| *L. reuteri* CP3019 | CP3019 | 49.6 | 2.2 | 0.000 |
| *L. oris* T | JCM11028 | 42.7 | 8.3 | 0.000 |
| *L. mucosae* T | JCM12515 | 44.0 | 4.9 | 0.000 |

TABLE 14

| Hexanal | Strain name | Residual ratio (%) | | |
| | | Average | Standard deviation | p-value (vs. L. gasseri T) |
| --- | --- | --- | --- | --- |
| uninoculated medium | — | 100.0 | 12.1 | 0.025 |
| *L. gasseri* T | JCM1131 | 69.8 | 2.3 | |
| *L. fermentum* T | JCM1173 | 14.9 | 2.1 | 0.000 |
| *L. fermntum* CP3024 | CP3024 | 18.1 | 2.4 | 0.000 |
| *L. fermentum* CP1299 | CP1299 | 22.6 | 7.5 | 0.001 |
| *L. reuteri* T | JCM1112 | 31.0 | 4.4 | 0.000 |
| *L. reuteri* CP3017 | CP3017 | 21.1 | 3.9 | 0.000 |
| *L. reuteri* CP3019 | CP3019 | 16.3 | 0.1 | 0.000 |
| *L. oris* T | JCM11028 | 20.7 | 1.6 | 0.000 |
| *L. mucosae* T | JCM12515 | 21.8 | 3.4 | 0.000 |

It could be confirmed that the amounts of aldehydes were significantly reduced by particular bacterial strains compared to the case of the control, *Lactobacillus gasseri* T.

Example 3

Figure 15:
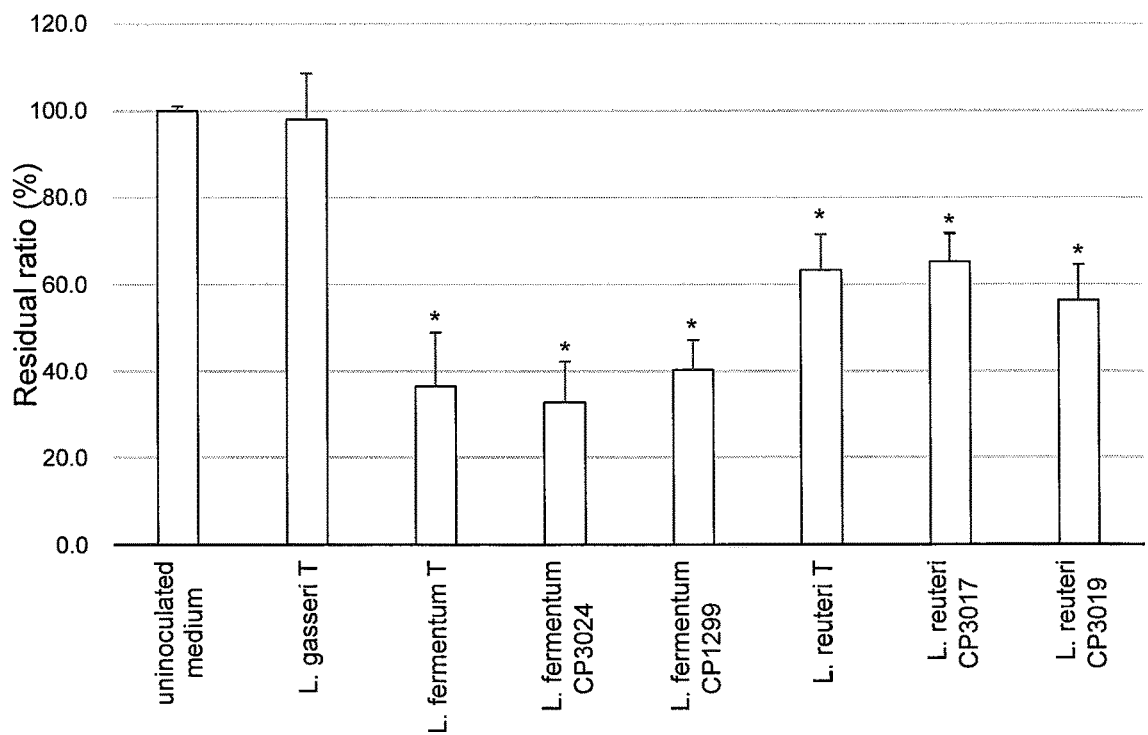
FIG. 15 is a graph showing the abilities of lactic acid bacteria to reduce the amount of benzaldehyde contained in a plant-based milk derived from barley.
Figure 16:
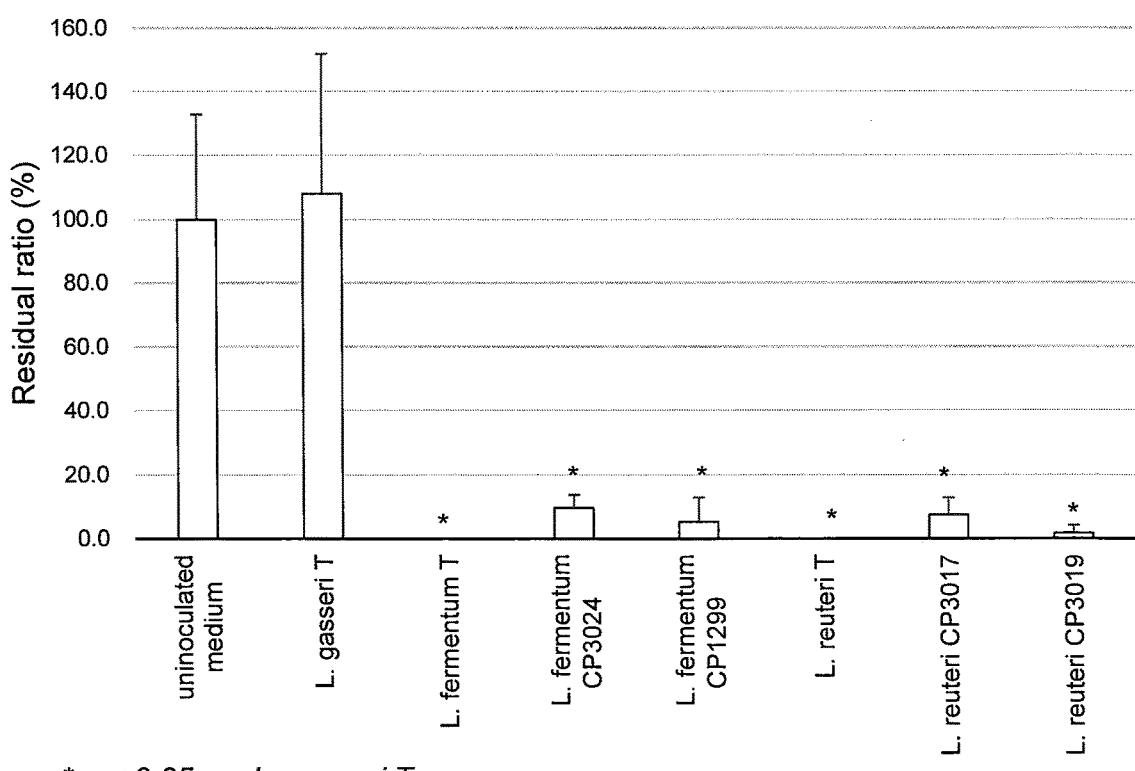
FIG. 16 is a graph showing the abilities of lactic acid bacteria to reduce the amount of 2,4-decadienal contained in a plant-based milk derived from barley.

As lactic acid bacteria, the bacterial strains shown in Table 15 and Table 16 were provided. Using MRS Medium (manufactured by BD Japan) supplemented with 0.05% by mass cysteine hydrochloride, each lactic acid bacterium was cultured in an environment at 37° C. under anaerobic conditions for 16 hours, to prepare a preculture of each lactic acid bacterial strain. A commercially available barley flour (Oomugi-club; material: whole grain flour) and pure water were mixed together at a weight ratio of 2:8, and amylase (manufactured by Novozymes, BAN480L) was added thereto at 0.02% by volume. Thereafter, the mixture was allowed to react with stirring at 60° C. for 6 hours, and then sterilized at 95° C. 15 minutes to provide a barley milk medium. To the barley milk medium, the preculture of the lactic acid bacterium was added at 5% by volume, and static culture was performed in an environment at 37° C. for 16 hours, to obtain a culture as a plant-based milk-fermented liquid. The concentration of each of benzaldehyde and 2,4-decadienal contained in the resulting culture was quantified by a modification of the LC-MS/MS method described in Drug Test. Analysis, 8, 458-464 (2016). Details of the quantification method are described later. The residual ratio (%) of each aldehyde was calculated by dividing the concentration of the aldehyde in each culture by the average of the concentration of the aldehyde in the uninoculated medium, and multiplying the resulting value by 100. The results are shown in Table 15 and Table 16, and FIG. 15 and FIG. 16. For statistical processing, the Student t-test was used. The test was carried out based on comparison with the residual ratio in the case of *Lactobacillus gasseri* T. The sample data number (n number) was set to 3. A significant difference was assumed at a level of P<0.05.

TABLE 15

| Bezaldehyde | Strain name | Residual ratio (%) | | |
| | | Average | Standard deviation | p-value (vs. L. gasseri T) |
| --- | --- | --- | --- | --- |
| uninoculated medium | — | 100.0 | 1.0 | 0.798 |
| *L. gasseri* T | JCM1131 | 98.0 | 10.6 | |
| *L. fermentum* T | JCM1173 | 36.5 | 12.3 | 0.006 |
| *L. fermentum* CP3024 | CP3024 | 32.8 | 9.4 | 0.003 |
| *L. fermentum* CP1299 | CP1299 | 40.3 | 6.8 | 0.003 |
| *L. reuteri* T | JCM1112 | 63.3 | 8.3 | 0.022 |
| *L. reuteri* CP3017 | CP3017 | 65.2 | 6.5 | 0.020 |
| *L. reuteri* CP3019 | CP3019 | 56.3 | 8.3 | 0.012 |

TABLE 16

| 2,4-Decadienal | Strain name | Residual ratio (%) | | |
| | | Average | Standard deviation | p-value (vs. L. gasseri T) |
| --- | --- | --- | --- | --- |
| uninoculated medium | — | 100.0 | 32.8 | 0.844 |
| *L. gasseri* T | JCM1131 | 108.1 | 43.7 | |
| *L. fermentum* T | JCM1173 | 0.0 | 0.0 | 0.025 |
| *L. fermentum* CP3024 | CP3024 | 9.7 | 4.1 | 0.034 |
| *L. fermentum* CP1299 | CP1299 | 5.4 | 7.6 | 0.031 |
| *L. reuteri* T | JCM1112 | 0.0 | 0.0 | 0.025 |
| *L. reuteri* CP3017 | CP3017 | 7.4 | 5.4 | 0.032 |
| *L. reuteri* CP3019 | CP3019 | 1.7 | 2.5 | 0.026 |

It could be confirmed that the amounts of aldehydes were significantly reduced by particular bacterial strains compared to the case of the control, *Lactobacillus gasseri* T.

Method of Quantifying Aldehydes

Hexanal d-12 (manufactured by Sigma-Aldrich) was used alone as an internal standard. An internal standard solution was prepared by dissolving hexanal d-12 at a concentration of 25 ng/µl in 50% by volume aqueous ethanol solution. After mixing 40 µl of the internal standard solution, 80 µl of a solution prepared by dissolving dibutylhydroxytoluene (manufactured by Tokyo Chemical Industry Co., Ltd.) at a concentration of 1 mg/ml in 100% by volume ethanol, 440 µl of 100% by volume ethanol, and 440 µl of a culture supernatant or culture for which aldehydes were to be quantified, the resulting mixture was centrifuged at an acceleration of 3700 g for 10 minutes, followed by collecting 750 µl of the supernatant. After mixing 325 µl of this supernatant with 325 µl of a solution prepared by dissolving 2,4-dinitrophenylhydrazine hydrochloride (manufactured by Tokyo Chemical Industry Co., Ltd.) at a concentration of 0.05 mol/l in the mixed solvent "acetonitrile:acetic acid:pure water=80:10:10 (volume ratio)", the resulting mixture was allowed to react in an environment at 60° C. for 2 hours. Thereafter, the resulting reaction product was mixed with 1 ml of pure water, and then liquid-liquid extraction was carried out a total of four times using 500 µl of hexane. The hexane solution obtained by the liquid-liquid extraction was dried and solidified using a centrifugal evaporator, and the dried and solidified product was dissolved in 1 ml of the mixed solvent "0.03% by volume aqueous acetic acid solution:acetonitrile=60:40 (volume ratio)". The resulting solution was subjected to high-performance liquid chromatography (HPLC) as a derivatized sample.

As a column and a guard column for the HPLC, an Atlantis T3 C18 column (3 µm, 2.1×150 mm), manufactured by Waters, and an Atlantis guard column T3 C18 (3 µm, 2.1×10 mm), manufactured by Waters, were used according to the method described in Drug Test. Analysis, 8, 458-464 (2016). For a modified LC-MS/MS equipment, the Nextera HPLC system (communication bus module: CBM-20A; pump: LC-30AD; autosampler: SIL-30AC; degasser: DGU-20A5R; column oven: CTO-20AC), manufactured by Shimadzu Corporation, was used as a high-performance liquid chromatography (HPLC) system, and Sciex Triple quad 6500+, manufactured by AB SCIEX, was used as a tandem mass spectrometry (MS/MS) system.

The following modified conditions were used for the LC-MS/MS. As mobile phase A, 0.03% by volume aqueous acetic acid solution was used. As mobile phase B, 100% by volume acetonitrile was used. At the beginning, "mobile phase A:B=60:40 (volume ratio)" was used as the initial concentration. Two minutes later, the concentration was set to "mobile phase A:B=52:48 (volume ratio)", and this condition was maintained for 37 minutes. Four minutes thereafter, the concentration was set to "mobile phase A:B=0:100 (volume ratio)", and this condition was maintained for 8 minutes. The sample injection volume for the HPLC was 1 μl. Modified conditions commonly employed for the compounds were as shown in Table 17 below, and modified conditions specifically employed for each compound were as shown in Table 18 below.

TABLE 17

| Curtain gas (psi) | Collision activated dissociation gas (psi) | Ion spray voltage floating (volts) | Temperture (° C.) | Ion source gas1 (psi) | Ion source gas2 (psi) | Entrance potential (volts) |
|---|---|---|---|---|---|---|
| 30 | 8 | −4500 | 500 | 30 | 70 | −10 |

TABLE 18

| | Declustering potential (volts) | Collision energy (volts) | Collision cell exit potential (volts) | Elution time (min) | Precusor ion (m/z) | Product ion (m/z) |
|---|---|---|---|---|---|---|
| Benzaldehyde | −35 | −20 | −13 | 31.3 | 284.8 | 162.8 |
| Hexanal d-12 | −5 | −20 | −1 | 45.6 | 291.0 | 163.1 |
| Hexanal | −35 | −32 | −11 | 45.7 | 278.9 | 152.0 |
| 2-Methylpropanal | −40 | −16 | −11 | 25.5 | 251.0 | 162.8 |
| 3-Methylbutanal | −5 | −26 | −11 | 37.2 | 264.9 | 152.1 |
| 2,4-Decadienal | −40 | −26 | −19 | 47.7 | 331.0 | 180.9 |
| 2-Methylbutanal | −25 | −18 | −13 | 38.6 | 265.0 | 100.9 |
| 2,4-Nonadienal | −5 | −24 | −9 | 47.2 | 317.0 | 181.1 |

Based on the above conditions, a quantitative method was established in the multiple reaction monitoring mode using hexanal d-12 as an internal standard. Benzaldehyde (manufactured by Tokyo Chemical Industry Co., Ltd.), hexanal (manufactured by Tokyo Chemical Industry Co., Ltd.), 2-methylpropanal (manufactured by Tokyo Chemical Industry Co., Ltd.), 3-methylbutanal (manufactured by Tokyo Chemical Industry Co., Ltd.), 2,4-decadienal (manufactured by Tokyo Chemical Industry Co., Ltd.), 2-methylbutanal (manufactured by Tokyo Chemical Industry Co., Ltd.), and 2,4-nonadienal (manufactured by Tokyo Chemical Industry Co., Ltd.) were derivatized under the conditions described above, to prepare calibration curves for the aldehydes. Thereafter, the aldehydes contained in the culture or culture supernatant were derivatized under the above conditions, and the concentrations of the aldehydes contained in the culture supernatant (Reference Examples 3 to 6) or in the culture (Examples 1 to 3) were quantified.

The disclosure of Japanese patent application No. 2021-052277 (filing date: Mar. 25, 2021) is incorporated herein by reference in its entirety. All documents, patent applications, and technical standards cited in the present description are incorporated herein by reference to the same extent as in cases where the individual documents, patent applications, and technical standards are specifically and individually described to be incorporated by reference.

Accession Numbers

NITE BP-1512
NITE BP-03426
NITE BP-03427
NITE BP-03428

The invention claimed is:

1. A method for producing a plant-based milk-fermented liquid, the method comprising bringing a plant-based milk into contact with a lactic acid bacterial strain(s) including at least one selected from the group consisting of the *Lactobacillus fermentum* CP1299 strain, the *Lactobacillus fermentum* CP3024 strain, the *Lactobacillus reuteri* CP3017 strain, and the *Lactobacillus reuteri* CP3019 strain.

2. The method for producing a plant-based milk-fermented liquid according to claim 1, wherein the plant-based milk is derived from a cereal.

3. The method for producing a plant-based milk-fermented liquid according to claim 1, wherein the plant-based milk is derived from at least one selected from the group consisting of rice and barley.

4. The method for producing a plant-based milk-fermented liquid according to claim 1, wherein the plant-based milk is a saccharified plant-based milk.

5. The method for producing a plant-based milk-fermented liquid according to claim 1, wherein the contact between the lactic acid bacterial strain(s) and the plant-based milk comprises fermentation of the plant-based milk by the lactic acid bacterial strain(s).

6. The method for producing a plant-based milk-fermented liquid according to claim 1, wherein the plant-based milk is a product prepared by size reduction and liquefaction of a plant material by physical crushing and/or saccharification.

\* \* \* \* \*